(12) United States Patent
Wu et al.

(10) Patent No.: US 8,389,625 B2
(45) Date of Patent: Mar. 5, 2013

(54) PRODUCTION OF SYNTHETIC HYDROCARBON FLUIDS, PLASTICIZERS AND SYNTHETIC LUBRICANT BASE STOCKS FROM RENEWABLE FEEDSTOCKS

(75) Inventors: Margaret May-Som Wu, Skillman, NJ (US); Karla Schall Colle, Houston, TX (US); Ramzi Yanni Saleh, Baton Rouge, LA (US); Allen D. Godwin, Seabrook, TX (US); Jon Edmond Randolph Stanat, Houston, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 366 days.

(21) Appl. No.: 12/653,742

(22) Filed: Dec. 17, 2009

(65) Prior Publication Data

US 2010/0160506 A1    Jun. 24, 2010

Related U.S. Application Data

(60) Provisional application No. 61/203,523, filed on Dec. 23, 2008.

(51) Int. Cl.
*C08K 5/09* (2006.01)
(52) U.S. Cl. ......................................................... 524/773
(58) Field of Classification Search ................... 524/773
See application file for complete search history.

(56) References Cited

U.S. PATENT DOCUMENTS

| | | |
|---|---|---|
| 3,149,178 A | 9/1964 | Hamilton et al. |
| 3,382,291 A | 5/1968 | Brennan |
| 3,742,082 A | 6/1973 | Brennan |
| 3,780,128 A | 12/1973 | Shubkin |
| 3,833,678 A | 9/1974 | Brennan |
| 3,997,621 A | 12/1976 | Brennan |
| 4,172,855 A | 10/1979 | Shubkin et al. |
| 4,303,590 A | 12/1981 | Tanaka et al. |
| 4,545,941 A | 10/1985 | Rosenburg |
| 4,827,064 A | 5/1989 | Wu |
| 4,827,073 A | 5/1989 | Wu |
| 4,956,122 A | 9/1990 | Watts et al. |
| 5,354,878 A | 10/1994 | Connemann et al. |
| 5,525,126 A | 6/1996 | Basu et al. |
| 5,833,721 A | 11/1998 | Hart et al. |
| 5,859,159 A | 1/1999 | Rossi et al. |
| 5,958,849 A | 9/1999 | Hewson et al. |
| 6,270,538 B1 | 8/2001 | Ledeore et al. |
| 6,410,812 B1 | 6/2002 | Hope et al. |
| 6,706,828 B2 | 3/2004 | DiMaio |
| 6,949,688 B2 | 9/2005 | Goze et al. |
| 7,022,784 B2 | 4/2006 | Wu |
| 7,041,864 B2 | 5/2006 | Fong et al. |
| 7,456,329 B2 | 11/2008 | Wu et al. |
| 2002/0010359 A1 | 1/2002 | Kaita et al. |
| 2003/0149289 A1 | 8/2003 | Suppes |
| 2005/0070450 A1 | 3/2005 | Roby et al. |
| 2007/0131579 A1 | 6/2007 | Koivusalmi et al. |
| 2007/0142242 A1 | 6/2007 | Gleeson et al. |
| 2007/0179307 A1 | 8/2007 | Olivier-Bourbigou et al. |
| 2007/0197772 A1 | 8/2007 | Arora et al. |
| 2007/0249796 A1 | 10/2007 | Arai et al. |

FOREIGN PATENT DOCUMENTS

| | | |
|---|---|---|
| EP | 0 508 418 | 8/1995 |
| WO | WO 99/67347 | 12/1999 |
| WO | WO 02/14384 | 2/2002 |
| WO | WO 2007/011462 | 1/2007 |
| WO | WO 2007/050071 | 5/2007 |
| WO | WO 2007/111776 | 10/2007 |

OTHER PUBLICATIONS

F. B. H. Ahmad et al., "Co-Metathesis Reaction of Crude Palm Oil and Ethene", Journal of the American Oil Chemists' Society Pub. No. 72(6), 757-758 (1995).
J. C. Mol, "Catalytic Metathesis of Unsaturated Fatty Acid Esters and Oils", Topics in Catalysis, vol. 27, Nos. 1-4 (Feb. 2004).
A. D. Godwin, "Plasticizers", Applied Polymer Science 21st Century, ed. by C. D. Craver and C. E. Carraher, Elsevier (2000), pp. 157-175.
E. B. Cahoon, "Genetic Enhancement of Soybean Oil for Industrial Uses: Prospects and Challenges", USDA Research Service, AgBioForum 6.
American Soybean Association website, found on the internet at http://www.unitedsoybean.org/soystats2001.
T. Buhr et al., "Ribozyme termination of RNA Transcripts Down-Regulate Seed Fatty Acid Genes in Transgenic Soybean", Plant Journal, 30, pp. 155-163.
D. A. Burg et al., "Preparation of Meadowfoam Dimer Acids and Dimer Esters and Their Use as Lubricants", Journal of the American Oil Chemists Society, 68, pp. 600-603.
E. B. Cahoon et al., "Substrate-Dependent Mutant Complementation to Select Fatty Acid Desaturase Variants, etc.", Proceedings of the Nat'l Acad of Sci, 97, 12350-12355.
E. B. Cahoon et al., "Production of Fatty Acid Components of Meadowfoam Oil in Somatic Soybean Embryos", Plant Physiology, 124, 243-251.

(Continued)

*Primary Examiner* — Edward Cain
(74) *Attorney, Agent, or Firm* — Robert A. Migliorini (57) ABSTRACT

This disclosure is directed to an integrated method for making synthetic hydrocarbon fluids, plasticizers and polar synthetic lubricant base stocks from a renewable feedstock. More particularly, the disclosure is directed to a metathesis reaction of natural oil or its derivative ester and ethylene in the presence of an effective amount of a metathesis catalyst to form linear alpha-olefins, internal olefins and reduced chain length triglycerides. The linear alpha-olefins and/or internal olefins are polymerized to produce synthetic hydrocarbon fluids in the presence of a suitable catalyst. The reduced chain length triglycerides are converted into polar synthetic lubricant base stocks or plasticizers by hydrogenation, isomerization, followed by hydrogenations, or by hydroisomerization processes. Alternatively, the reduced chain length triglycerides can also be epoxidized to form epoxidized triglyceride plasticizers, optionally followed by carbonation, to form carbonated triglyceride plasticizers.

19 Claims, 4 Drawing Sheets

OTHER PUBLICATIONS

E. B. Cahoon et al., "Formation of conjugated delta 8, delta 10 double bonds by delta 12-oleic acid desaturase, etc.", J. Biol. Chem., 276, 2637-2643.

E. B. Cahoon et al., "Transgenic production of epoxy fatty acids by expression of a cytochrome P450 enzyme", etc., Plant Physiology, 128, 615-624.

L. Crandall, "Bioplastics: A burgeoning industry", Inform, 13, 626-630 (2002).

S. M. Erhan et al., "Estolides from meadowfoam oil fatty acids, etc", Journal of the American Oil Chemists Society, 70, 460-465 (1993).

A. J. Kinney, "Genetic engineering of oilseeds for desired traits", Genetic engineering, vol. 19 (pp. 149-166), Plenum Press (1997).

W. A. Parrot et al., "Transgenic soybean", Soybeans: Improvement, Production and Uses (3rd ed.), Agronomy Monograph No. 16, Madison, WI, Am Soc of Agronomy.

Process Economics Program Report 251, "Biodiesel Production", Stanford Research Institute (SRI), 2004.

T. M. Trnka et al., "The Development of L2X2Ru=CHR Olefin Metathesis Catalysts: An Organometallic Success Story", Acc. Chem. Res., 2001, 34, 18-29.

A. Furstner, "Olefin metathesis and beyond", Agnew. Chem., Int. Ed., 2000, 39, 3012-3043.

E. L. Dias et al., "Well-Defined Ruthenium Olefin Metathesis Catalysts: Mechanism and Activity", Am. Chem. Soc., 1997, 119, 3887-3897.

M. Scholl et al., Increased ring closing metathesis activity of ruthenium-based catalysts, etc., Tetrahedron Lett., 1999, 40, 2247-2250.

T. Weskamp et al., "A novel class of ruthenium catalysts for olefin metathesis", Angew. Chem., Int. Ed., 1998, 37, 2490-2493.

A. K. Chatterjee, "Olefin Cross-Metathesis", Handbook of Metathesis, vol. 2, G. H. Grubbs (ed.), 2003, Wiley-Verlag GmbH & Co. KGaA, Weinheim, p. 246.

J. C. Mol, "Catalysts for Homogeneous Metathesis of Functionalized Olefins", Olefin Metathesis and Polymerization Catalysts, etc., NATO Adv. Sci. Inst. Series, p. 115.

J.C. Mol, Olefin Metathesis over Supported Rhenium Oxide Catalysts, Catalysis Today, 51, 1999, 289-299.

H. K. Shoba and K. Kishore, Structural Expressions of Long-Chain Esters on Their Plasticising Behavior in Poly(vinyl chloride), Macromolecules, 1992, 25, 6765-6769.

B. Tamami, S. Sohn and G. L. Wilkes, J. Appl. Poly. Sci., 2004, 92(2), 883-891.

J. Sears and J. Darbey, "The Technology of Plasticizers", John Wiley & Sons, New York, 1982, pp. 95-99.

P. A. Small, "Some Factors Affecting the Solubility of Polymers", J. Appl. Chem., 3, pp. 76-80 (1953).

PRODUCTION OF SYNTHETIC HYDROCARBON FLUIDS, PLASTICIZERS AND SYNTHETIC LUBRICANT BASE STOCKS FROM RENEWABLE FEEDSTOCKS

CROSS-REFERENCE TO RELATED APPLICATIONS

This application claims priority to U.S. Provisional Application Ser. No. 61/203,523 filed Dec. 23, 2008, herein incorporated by reference in its entirety.

FIELD

The present disclosure relates to an integrated method of producing synthetic hydrocarbon fluids, plasticizers and synthetic lubricant base stocks from renewable feedstocks.

BACKGROUND

Recently, due to the high petroleum price and the unstable nature of the oil supply, there is a strong incentive to produce fuels and chemical products from renewable feedstocks. Development and marketing of biodiesel and bioethanol fuels are in high gear. Bio-diesel fuel made from plant oils and bio-ethanol made from corn or sugar plants are already in the market and are expected to grow at fast rates. To support this growth, a large amount of well-priced natural oils and ethanol are expected to become available. These natural oils have chemical compositions unsuitable for high performance product application.

Natural oils, especially plant oils, are unsuitable for high performance synthetic lubricant base stock application or polymer plasticizers, such as plasticized or flexible polyvinyl chloride (PVC) products. This is because natural oils contain high amounts of triglycerides of unsaturated fatty acids. The high amount of unsaturation and the high amount of long chain fatty acids contribute to the poor oxidative stability, poor low temperature properties and poor plasticization properties. Heretofore known, synthetic lubricant base stocks or plasticizers have excellent performance. However, they are all derived from non-renewable petroleum feedstock.

Triglycerides are the major component in naturally occurring fats and oils. A triglyceride is the condensation product of one molecule of glycerol with three molecules of fatty acids to yield three molecules of water and one molecule of triglyceride. A fatty acid is an aliphatic compound containing 4 to 24 carbon atoms and having a terminal carboxyl radical. Naturally occurring fatty acids, with only some exceptions, have an even number of carbon atoms and, if any unsaturation is present, the first double bond is generally located between the ninth and tenth carbon atoms. The characteristics of the triglycerides are strongly influenced by the nature of their fatty acid radicals. For a detailed description of triglycerides refer to U.S. Pat. No. 4,545,941, incorporated herein by reference.

Alpha-olefins are primarily used as intermediates in the production of polyolefins, chemicals, and consumer products. For example, 1-propene is used to make polypropylene, acrylonitrile, propylene oxide, and isopropyl alcohol. The major uses of 1-butene are to produce poly(1-butene) and various four carbon aldehydes and alcohols. The higher alpha-olefins and internal olefins are commonly used in the manufacture of synthetic lubricating oils, detergents, plasticizer alcohols, flavors, perfumes, dyes, pharmaceuticals, and resins. The major commercial source of alpha-olefins is petroleum. Alpha-olefins and internal olefins can be produced through a cross-metathesis reaction of renewable feedstocks with an alkene, such as ethylene, in the presence of a metathesis catalyst.

U.S. Pat. No. 4,545,941, discloses production of certain alpha-olefins by reacting triglycerides having fatty acid esters containing isolated carbon-carbon double bonds with ethylene at an ethylene partial pressure of about 200-550 psig in the presence of a metathesis catalyst, specifically a catalyst comprising a tungsten compound and a tin compound (e.g. tungsten hexachloride tetramethyl tin). The reaction is carried out at a temperature of 100° F. to 500° F.

Ahmad et al., Co-Metathesis Reaction of Crude Palm Oil and Ethene, Journal of the American Oil Chemists' Society Pub. No. 72(6), 757-8 (1995), discloses the co-metathesis reaction of crude palm oil with ethene in the presence of tungsten hexachloride and tetramethyl tin $WCl_6Me_4Sn$, followed by termination of this reaction with methanol, which gives terminal alkenes. The major metathesis products are 1-decene and Me 9-decenoate.

The first successful metathesis conversion in the field of unsaturated fatty acid esters and oils was performed in 1972 by Boelhouwer and coworkers, viz., the selective transformation of methyl oleate (methyl cis-9-octadecenoate), a readily available unsaturated ester, into equimolar amounts of 9-octadecene and dimethyl 9-octadecene-1,18-dioate, in the presence of the catalyst system $WCl_6/(CH_3)_4Sn$. Catalytic metathesis of unsaturated fatty acid esters and oils is described in J. C. Mol, Catalytic Metathesis of Unsaturated Fatty Acid Esters and Oils, Topics in Catalysts Vol. 27, Nos. 1-4 (February 2004), which is incorporated herein by reference.

U.S. Patent Publication No. 2007/0179307 discloses a process for co-producing an olefinic fraction and a composition of diacids or diesters of fats. The process comprises, in succession: a) metathesis of an unsaturated fat with ethylene in the presence of a metathesis catalyst and at least one non-aqueous ionic liquid; b) separating and recycling the ionic liquid used in the first step; c) separating, by distillation, the olefinic fraction (fraction A) from the unsaturated fat monoester or mono-basic acid fraction (fraction B) formed in step a); d) homometathesis of the mono-unsaturated fat ester or acid cut (fraction B) which allows the co-production of unsaturated fat diesters or diacids (fraction C) and ethylene which is recycled to the first methathesis step of the process; and e) optionally, recycling the ionic liquid containing the catalyst used in step d). Particularly preferred starting material is an oleic sunflower seed oil, an oleic rapeseed oil or mono-alcohol esters of said oils, whereupon the process can produce both an olefinic fraction (mainly composed of 1-decene) and a composition of diesters or diacids wherein, in general, over half of the chains is constituted by unsaturated $C_{18}$ chains (mainly composed of octadecene-9 1,18-diacid or diester). The ethylene employed is recycled to the first methathesis step.

Poly alpha-olefins (PAOs) comprise a class of hydrocarbons manufactured by the catalytic oligomerization (polymerization to low-molecular-weight products) of linear alpha-olefin (LAO) monomers. LAOs typically range from 1-octene to 1-dodecene, with 1-decene being a preferred material, although oligomeric copolymers of lower olefins such as ethylene and propylene may also be used, including copolymers of ethylene with higher olefins as described in U.S. Pat. No. 4,956,122 and the patents referred to therein.

Some PAO products have achieved importance in the lubricating oil market. Specifically, PAOs may be produced by the polymerization of olefin feed in the presence of a catalyst such as $AlCl_3$, $BF_3$, or promoted $AlCl_3$, $BF_3$, or metallocene catalyst systems promoted by a non-coordinating anion or methylaluminoxane. PAOs of different viscosity grades are typically produced using promoted $BF_3$ or $AlCl_3$ catalysts. Processes for the production of PAOs are disclosed, for example, in the following patents: U.S. Pat. Nos. 3,997,621; 6,949,688; 3,833,678; 6,410,812; 3,997,621; 6,949,688; 3,149,178; 3,382,291; 3,742,082; 3,780,128; 4,172,855; 4,956,122; WO 2007/111,776; and WO 2007/011,462, which are incorporated by reference.

Several publications propose polymerization of various alpha-olefins, at least some in the presence of metallocene catalyst systems, to provide polymers having various utilities, such as lubricant components. For example, WO 2007/011462 discusses a process for producing PAOs of high viscosity index (HVI-PAOs), including contacting a feed comprising a mixture of LAOs with an activated metallocene catalyst to produce liquid polymers for use in lubricant components or as functional fluids. The copolymer composition may be made from at least two different alpha-olefins of $C_3$ to $C_{30}$ range, with monomers randomly distributed in the polymers. In an embodiment, one of the monomers is a higher alpha-olefin, such as one chosen from $C_{12}$ to $C_{18}$ alpha-olefins, and the second one or more alpha-olefin is, e.g., chosen from $C_3$ to $C_7$ alpha-olefins. In another embodiment there are used propylene or 1-butene as one of the feed components, as they are readily available from refinery or petrochemical plants. The resulting copolymers are said to have useful lubricant properties, including excellent VI, pour point, low temperature viscometrics by themselves or as a blend fluid with other lubricants or polymers.

Efforts have been made to prepare various PAOs using metallocene catalyst systems. Examples include U.S. Pat. No. 6,706,828, which discusses production of PAOs in the presence of meso-forms of certain metallocene catalysts under high hydrogen pressure with methyl alumoxane as an activator. WO 02/14384 and WO 99/67347 discuss similar topics.

U.S. Pat. No. 5,859,159 is directed to a dilute process for the polymerization of non-ethylene, alpha-olefin homopolymers and copolymers in the presence of metallocene catalyst systems. The alpha-olefin feed stream used in the process comprises at least one alpha-olefin, such as propylene, 1-butene, pentene-1,4-methyl-pentene-1, hexene-1, octene-1 and higher alpha-olefins up to and including nanodecene-1, e.g., mixtures of propylene and butene-1. The polymers of most of the examples have isotactic index of at least 80%. The product can be used as a backbone for production of lubricants, or oil dispersants and viscosity modifiers.

Plasticizers are incorporated into resins to increase the flexibility, workability, or distensibility of the resins. The largest use of plasticizers is in the production of plasticized or flexible PVC products. Typical uses of plasticized PVC products include films, sheets, tubing, coated fabrics, wire and cable insulation and jacketing, adhesives, sealants, inks, and medical products, such as blood bags and tubing, and similar articles. Other polymer systems that use small amounts of plasticizers include polyvinyl butyral, acrylic polymers, nylon, polyolefins, polyurethanes, and certain fluoroplastics. A listing of the major plasticizers and their compatibilities with different polymer systems is provided in "Plasticizers," A. D. Godwin, in Applied Polymer Science 21$^{st}$ Century, edited by C. D. Craver and C. E. Carraher, Elsevier (2000); pp. 157-175.

Natural triglycerides from various vegetable oils have been tried as plasticizers in the past but have compatibility issues. The alkyl groups on these natural triglycerides are linear, and the alkyl chain is too long to have good compatibility. Soybean oil has been epoxidized (ESO) to try to improve its compatibility and performance as a plasticizer. Even with the polarity of the epoxide group, ESO has long term compatibility issues due to the long alkyl chains (C16-C18). It is generally used as a PVC stabilizer rather than a plasticizer. Stabilizers are used at much lower concentrations than plasticizers.

SUMMARY

A first embodiment of the present disclosure is directed to an integrated method for making oligomeric synthetic hydrocarbon fluids, polar functional fluids or a combination thereof, which comprises contacting a feed selected from one or more natural oil which includes triglyceride esters, one or more mono-ester derived from one or more triglyceride, or a mixture thereof, with ethylene or another alkene in the presence of an effective amount of a metathesis catalyst. Each of the natural oils and mono-esters includes linear $C_{12}$ to $C_{30}$ unsaturated fatty acid moieties. The contacting step produces linear alpha-olefins (LAO), internal olefins and reduced chain length triglycerides, and/or reduced chain length mono-esters derived from triglycerides. Subsequently, the linear alpha-olefins, the internal olefins or a mixture thereof is polymerized in the presence of a suitable catalyst to produce one or more oligomeric synthetic hydrocarbon fluids. Suitable catalysts include $AlCl_3$, $BF_3$, promoted $AlCl_3$, $BF_3$, or metallocene catalyst systems promoted by a non-coordinating anion (NCA) or methylaluminoxane (MAO). Further, the reduced chain length triglycerides may be converted into synthetic polar lubricant base stocks or plasticizers by a hydrogenation process, by isomerization followed by hydrogenation, or by a hydroisomerization process.

A second embodiment of the present disclosure is directed to an integrated method for making epoxidized triglyceride plasticizers comprising contacting at least one natural oil, which includes one or more triglyceride, with ethylene in the presence of an effective amount of a metathesis catalyst to form linear alpha-olefins, internal olefins, and reduced chain length triglyceride or triglycerides. The reduced chain length triglyceride or triglycerides of the second embodiment may be oxidized to form epoxidized triglyceride plasticizers. If need be, additional polarity may be incorporated into the reduced chain length triglycerides prior to the oxidation. Optionally, the epoxidized triglyceride plasticizers may be carbonated to produce carbonated triglyceride plasticizers.

These and other features and attributes of the integrated method of producing synthetic hydrocarbon fluids, plasticizers and synthetic lubricant base stocks from renewable feedstocks of the present disclosure and their advantageous applications and/or uses will be apparent from the detailed description which follows.

BRIEF DESCRIPTION OF THE DRAWINGS

To assist those of ordinary skill in the relevant art in making and using the subject matter hereof, reference is made to the appended drawings, wherein.

DETAILED DESCRIPTION

Provided herein are integrated methods for making synthetic hydrocarbon fluids, plasticizers and synthetic polar lubricant base stocks from renewable feedstocks.

All numerical values in this disclosure are understood as being modified by "about" or "approximately" the indicated value, and take into account experimental error and variations that would be expected by a person having ordinary skill in the art. All singular forms of monomers, polymers or other components described herein including (without limitations) components of the compositions are understood to include plural forms thereof and vice versa.

Various embodiments and aspects of the disclosure will now be described in detail with reference to the accompanying figures. Still other aspects, features, and advantages of the disclosure are readily apparent from the entire description thereof, including the figures, which illustrate a number of exemplary embodiments and implementations. Furthermore, the terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

In this disclosure, whenever a composition, an element or a group of elements is preceded with the transitional phrase "comprising", it is understood that we also contemplate the same composition or group of elements with transitional phrases "consisting essentially of", "consisting", "selected from the group of consisting of", or "is" preceding the recitation of the composition, element, or elements and vice versa.

For purposes of all embodiments, the term "renewable feedstock" is synonymous with the term "natural oil" which includes plant oils and vegetable oils and animal oils, and/or $C_1$-$C_5$ alkyl ester or esters of fatty acids derived from plant oil, vegetable oil or animal oil. The plant or vegetable oil may also be referred to herein as "seed oil". As known in the art, plant oils may include corn oil, sugar cane oil, canola oil, sunflower oil, rapeseed oil, mustard oil, olive oil, peanut oil, soybean oil, cottonseed oil, palm kernel oil, palm oil, coconut oil, rice bran oil, linseed oil, fax seed oil, sesame oil, or any oil derived from plant or vegetable material, etc. Animal oil, animal fats or animal lard can also be used as a starting material. Examples include the glycerides derived from beef fats, pork fat or lard, chicken fats, goal or sheep fats, whale fats, suet fats, tallow fats, or any fats or oils derived from animal parts. In this disclosure, the term triglyceride (or triglycerides) is synonymous with triglyceride ester (or triglyceride esters).

It is notable that the metathesis reaction of triglyceride esters of all embodiments of this disclosure does not use a non-aqueous ionic liquid, which is required by U.S. Patent Pub. No. 2007/0179307.

I. First Embodiment

Advantageous starting natural oil or oils for the process of this embodiment should contain a relatively high amount of components having a single unsaturated double bond in the fatty acid (e.g., mono-unsaturated fatty acids). Examples of the mono-unsaturated fatty acids include cis-5-dodecenoic acid, myristoleic acid (cis-9-tetradecenoic acid, C14:1), palmitoleic (cis-9-hexadecenoic acid, C16:1), oleic acid (cis-9-octadecenoic acid, C18:1), gadoleic acid (cis-11-eicosenoic acid C20:1), eruric acid (cis-13-docosenoic acid C22:1). Although most natural occurring oils contain cis-isomers of fatty acids, their trans-analogs occurring naturally or via isomerization process during treatment, such as hydrogenation, can also be used. Other odd carbon number mono-unsaturated acids, cis- or trans-form, although rare in natural products, can also be used. Generally, oils rich in the cis-form of the mono-unsaturated acids are most abundant in natural oils especially plant-based oils, and are advantageous feeds. For example, canola oil, some rapeseed oil or some mustard oil includes 57%-60% monounsaturated fat, olive oil has about 75% monounsaturated fat while tea seed oil commonly includes over 80% monounsaturated fat. Oils which contain some di-unsaturated fatty acid moiety can also be used for this process. They can be converted to mono-alpha-olefins or di-olefins by the process described herein. These di-olefins can be separated from the mono-alpha-olefins or incorporated in the synthetic hydrocarbon products. For lube application, it may be advantageous to produce low amount of di-olefins from the metathesis step.

When choosing a feed from animal fats, it is advantageous to choose one that contains higher percentages of mono-unsaturated fatty acids and lower amounts of fully saturated fatty acid or multi-unsaturated fatty acid. Although animal fats, lard and oils can be used for this process, the yields to LAO and the final synthetic hydrocarbon base stocks may be lower than from plant-based oils because most animal fats, such as beef fat, pork fat, or suet, etc. contain higher amount of saturated fats than plant-based oils.

Freshly produced plant-based oils or animal-based fats/oils can be used as starting material. Used or treated plant oil or animal fats/oils can also be used as starting material. The used plant oils can be obtained from food preparation, cooking, or other processes that recover or recycle used plant oils or animal fats/oils. Many of the used plant oils may contain partially hydrogenated plant oils. Thus, they may contain the glycerides of the naturally occurring acids (mostly cis-acids) and also some glycerides of the corresponding isomerized trans-acids. These trans-acids of mono- or di-unsaturated acids are also suitable as feed for processes of this disclosure. In order to optimize product yields, the impurities in the used plant oils, such as water, decomposed products, sludges, carry-over component from the foods, etc. should be removed by pretreatments, known in the art, such as settlement and decantation, clarification, passing through drying column and similar procedures.

The rapeseed oils, canola oils, mustard oils or olive oils usually include triglycerides of long-chain fatty acids. In particular, suitable seed oils for this embodiment may include oils which have a significant amount of the glycerides of mono-unsaturated acids, such as myristoleic acid, palmitoleic, oleic, linoleic, gadoleic, behenic, eruric, and lauroleic acids, etc. These fatty acids are most suitable in conversion into desirable $C_5$ to $C_{14}$ linear alpha-olefins.

TABLE 1

Chemical Compositions of Plant Oils
Chemical Compositions of Plant Oils

BIODIESEL SOURCE COMPOSITIONS

| ($C_n$: no. of double bonds) | Soybean Oil wt % | Canola Oil wt % | Rapeseed Oil wt % | Sunflower Oil wt % |
|---|---|---|---|---|
| Myristic (14:0) | | | 0.1 | |
| Palmitic (16:0) | 11.0 | 3.9 | 2.8 | 6.1 |
| Palmitoleic (16:1) | 0.1 | 0.2 | 0.2 | |
| Stearic (18:0) | 4.0 | 1.9 | 1.3 | 5.3 |
| Oleic (16:1) | 23.4 | 64.1 | 23.8 | 21.4 |
| Linoleic (18:2) | 53.2 | 18.7 | 14.6 | 66.4 |
| Linolenic (18:3) | 7.8 | 9.2 | 7.3 | |
| Arachidic (20:0) | 0.3 | 0.6 | 0.7 | |
| Gadoleic (20:1) | | 1.0 | 12.1 | |
| Eicosadienoic (20:2) | | | 0.6 | |
| Behenic (22:0) | 0.1 | 0.2 | 0.4 | |
| Eruric (22:1) | | | 34.8 | |
| Others | | 0.2 | 1.3 | |

Fatty Acid Profile (carbon length: no. double bonds)

| Species | 16:0 Palmitic | 18:0 Stearic | 18:1 Oleic | 18:2 Linoleic | 18:3 Linolenic | 20:1 Gadoleic | 22:1 Eruric |
|---|---|---|---|---|---|---|---|
| Canola | 4.7 | 1.9 | 65.4 | 19.3 | 7.3 | 1.1 | 0.0 |
| Rapeseed | 2.5 | 0.7 | 11.4 | 10.6 | 9.1 | 5.4 | 55.7 |
| H. Mustard 1 | 4.1 | 3.1 | 40.3 | 7.8 | 1.7 | 6.4 | 25.5 |
| H. Mustard 2 | 2.5 | 2.4 | 56.3 | 5.5 | 2.2 | 4.5 | 20.7 |

Source: 251134

Soybean oil contains a relatively high amount of di-unsaturation in the form of linolenic acid in the fatty acid moiety. It can be used as a starting material for the process to produce alpha-olefins. After metathesis of the soybean oil with ethylene, the alpha-olefin fraction may contain a mixture of 1-octene, 1-decene and 1,3- or 1,4-di-olefins of $C_{11}$. These olefins can be used as a starting material for synthetic hydrocarbon synthesis. There are many reports of utilizing a modified soybean plant to produce soybean oil [e.g., Genetic enhancement of soybean oil for industrial uses: prospects and challenges, by Edgar B. Cahoon, USDA Research Service, AgBioForum 6 (1&2): 11-13. @2003 AgBioForum, and references therein, incorporated herein by reference,] with very high amount of oleic acid moiety, as high as 85% oleic acid content, vs. 25% oleic acid content made from traditional, i.e., naturally occurring, soybean plant. Such modified soybean plant with high oleic content is advantageously used as a feed in the process described herein.

In addition to the plant oils or animal fats/oils that can be used for this process, the fatty acid derivatives from plant oils or animal fats/oils can also be used. Examples of the derivatives include mono-esters derived from triglycerides (also known as mono-esters of the fatty acid moieties of the triglycerides). Methods of making such derivatives are known in the art, e.g. see, Process Economic Program Report 251 "Biodiesel Production" by Stanford Research Institute (SRI) and/or U.S. patents and patent application publications nos. U.S. Pat. No. 4,303,590, U.S. Pat. No. 5,354,878, 2002/0010359, 2003/0149289, and U.S. Pat. No. 5,525,126, all incorporated herein by reference. It is believed that the derivatives, such as the mono-esters, are not suitable for the production of plasticizers in this embodiment. Further examples of such derivatives include methyl esters of these fatty acids, commonly known as fatty acid methyl ester (FAME) or biodiesel, ethyl esters, propylene esters, etc. or simple fatty acids. In this case, the derivative, such as the unsaturated methyl ester or fatty acid, can react with ethylene (or other lower alkenes, as described herein) in the presence of a metathesis catalyst to give desirable LAO and/or internal olefins. The other products are mostly methyl ester of a smaller fatty acid or a smaller fatty acid, plus some di-ester or di-acid. The reaction scheme is shown below. The LAO and/or internal olefins can be used for further conversion into synthetic hydrocarbon fluids.

-continued

Furthermore, mixtures of natural oils and the fatty acid derivatives may also be used as the feed.

Reacting Natural Oils or Their Derivatives with Lower Alkene in the Presence of Metathesis Catalyst For purposes of all embodiments, cross-metathesis and co-metathesis are synonymous, and include the metathesis reaction of triglycerides having long-chain fatty acid esters (e.g., $C_{16}$-$C_{22}$) with an alkene or a mixture of alkenes. Examples of the alkenes include ethylene, propylene, 1-butene, cis- or trans-2-butene, 1-pentene, cis- or trans-2-pentene, 3-pentenes, 1-hexene, 2-hexene, mixture of these olefins, such as mixed butenes containing 1- and 2-butenes, n-pentenes, n-hexenes, etc. The alkene fraction may contain other inert components. For example, $C_4$ stream from a refinery containing 1-, 2- and iso-butenes and n-butane and/or isobutene can be used. Other mixed streams containing mixtures of pentenes, and pentanes can also be used. Generally, when ethylene is used as the co-metathesis reagent, it favors the formation of LAO. When other alkenes (which may also be referred to herein as "olefin") are used, they usually produce a mixture of LAO and internal olefins. When internal olefins are used to co-metathesis with the triglycerides having long chain unsaturated fatty acids, the product olefins are mostly internal olefins. Usually, advantageous olefins for co-metathesis with a feed comprising natural oils (which include triglyceride esters) and/or mono-esters are lower olefins, such as ethylene, propylene or butenes. The feed comprising natural oils (which include triglyceride esters) and/or mono-esters may be referred to herein as "glycerides". Ethylene is most advantageous to generate LAO with highest catalyst reactivity, productivity and most desirable product quality. Propylene and butenes are also desirable olefins for co-metathesis for slightly different reasons. Propylene and butenes sometimes are more desirable for co-metathesis with the natural oils and/or mono-esters because they are readily condensable gases and can be dissolved in or be in close contact with the feed during reaction. Thus, higher concentration of propylene or butenes can be maintained in the metathesis mixture, to give more cross- or co-metathesis product between olefins and glycerides; and reducing the amount of self-metathesis of the glycerides, when it is more desirable to do so.

Generally higher alkene concentration in the reaction medium favors cross- or co-metathesis. When ethylene is used for co-metathesis, it is more desirable to run the reaction at higher pressure, and lower temperature and use high stirring rate to maximize the ethylene concentration in the reaction medium. When ethylene is used for co-metathesis with natural oils (containing triglycerides) and/or the fatty acid derivatives (such as methyl oleate or methyl linoleates) substantially constant ethylene pressure is maintained of greater than 1 atmosphere, greater than 100 psi, greater than 200 psi, greater than 500 psi, greater than 750 psi, greater than 1000 psi, or greater than 1500 psi. Usually the range of about 0 to about 3000 psig, or 200 psi to 1000 psi can be used. If appropriate, propylene, butenes and pentenes are advantageous for co-metathesis with glycerides. Usually the amount of the alkenes used is at least in equal molar ratio to the amount of unsaturation or double bonds in the glycerides or the fatty acid derivatives, such as esters, e.g., mono-esters. Usually, it is advantageous to have the molar ratio of the alkenes to unsaturated double bonds of greater than 1.5, or greater than 2, or greater than 3, or greater than 5. When excess alkenes are used in the co-metathesis, the un-reacted alkenes can be recycled and reused. Higher amount of alkenes in the reaction medium promotes co-metathesis. Lower amount of alkenes allows more self-metathesis of the triglyceride esters or the derivatives, such as mono-esters of the unsaturated long chain fatty acids. An excessive amount of olefins reduces reactor efficiency, requires large reactor, more catalyst, and may reduce overall process efficiency. Therefore, there is an optimum alkene concentration, which depends on the desirable degree of co-metathesis vs. self-metathesis, the process economics and product selectivity, etc. One skilled in the art may determine the appropriate alkene concentration without more than routine experimentation. Sometimes, it is also desirable to conduct the co-metathesis reaction to convert only part of the triglycerides or the fatty acid or the derivatives. In such case the molar ratio of olefin to unsaturation can be below 1, such as 0.9 or 0.7. Without being bound by any operability theory, it is believed that when an effective amount of an alkene is not present to affect a significant amount of a cross-metathesis reaction, the triglycerides having long-chain fatty acid esters may undergo a self-metathesis reaction and produce internal olefins. An excess of an alkene can force a substantially pure cross-metathesis reaction and suppress self-metathesis of the esters.

Triglycerides having long-chain fatty acid esters (e.g. $C_{16}$-$C_{22}$) can be shortened via a metathesis reaction with an alkene (e.g., ethylene, propylene, butenes, etc. and other alkenes, as discussed herein) in the presence of a metathesis catalyst (e.g., Grubbs catalyst) to produce a desired mix of components: (i) LAOs (e.g., $C_6$-$C_{12}$ alpha-olefins), in particular, a significant amount of 1-decene, which is in great demand; (ii) some amount of internal olefins (e.g., $C_{16}$-$C_{22}$ internal olefins, in particular, 9-octadecene); (iii) small amount of di-olefins (e.g., 1,4-octadiene, 1,4-decadiene and 1,4-dodecadiene); (iv) 1-hexene, 1-octene; and (v) reduced chain length triglycerides (e.g., $C_8$-$C_{14}$). The internal olefins that are produced in the metathesis reaction have the double bond placed substantially in the center of the carbon chain.

Metathesis Catalysts

Many metathesis catalysts are suitable for this process. For purposes of the first embodiment, the metathesis catalyst can be any one of the following catalysts: first generation Grubbs, second generation Grubbs and Hoveyda-Grubbs. Such catalysts are known in the art, e.g., see Acc. Chem. Res. 2001, 34, 18-29; Angew. Chem., Int. Ed., 2000, 39, 3012-3043; Am. Chem. Soc. 1997, 119, 3887-3897; Tetrahedron Lett. 1999, 40, 2247-2250; Angew. Chem., Int. Ed. 1998, 37, 2490-2493; U.S. Patent Pub. No. 2007/0249796; U.S. Patent Pub. No. 2007/0197772, all being incorporated herein by reference including relevant publications identified therein. Chemical formulae of such catalysts are set forth below. Other catalysts can be found in the chapter "Olefin Cross-Metathesis" by A. K. Chatterjee, p. 246 of Handbook of Metathesis, Vol. 2, G. H. Grubbs (Ed.), 2003 Wiley-VCH Verlag GmbH & Co. KGaA Weinheim, also incorporated herein by reference.

Formula 1. First Generation Grubbs Catalyst where Cy is cyclohexyl

Formula 2: Second Generation Grubbs Catalyst where Cy = cyclohexyl

Formula 3. Hoveyda-Grubbs Catalyst

Other common metathesis catalysts of tungsten and molybdenum families can also be used in this process. These catalysts are described in the Chapter "Catalysts for the Homogeneous Metathesis of Functionalized Olefins" by J. C. Mol, on p. 115 of the book "Olefin Metathesis and Polymerization Catalysts, Synthesis, Mechanism and Utilization", ed. by Y. Imamoglu, B. Zumreoglu-Karan and A. J. Amass, Proceedings of the NATO Advanced Science Institutes Series, Published by Kluwer Academic Publisher, Dordrecht, The Netherlands. Solid supported $Re_2O_7/Al_2O_3$ catalyst can also be used for this reaction. The solid catalyst is described by J. C. Mol, "Olefin Metathesis over Supported Rhenium Oxide Catalysts" Catalysis Today, 51 (1999) 289-299. Both of these publications are incorporated herein by reference. The metathesis catalyst may also be an activated $WCl_6$ or $MoCl_6$ or $TaCl_5$ or $Re_2O_7$ on a solid support. The solid support may be $Al_2O_3$, $ZrO_2$, $Ta_2O_5$, $SiO_2$, $WO_3$, or $SiO_2/Al_2O_3$. The catalyst may be activated by: (i) a compound of the formula $AlR_aX_b$, wherein R is $C_1$-$C_6$ alkyl, X is a halide or an alkoxide, a+b equals 3, and each of a and b is 1 to 3; or by (ii) a compound of the formula $SnR_cX_d$, wherein R is $C_1$-$C_6$ alkyl, X is a halide or an alkoxide, c+d equals 4, and each of c, d is 1 to 4. The metathesis catalyst may also include halides and organometallic compounds of tungsten, molybdum, ruthenium, tantalum, and rhenium.

Such a metathesis reaction is conducted between the temperature of 0° C. to 300° C., depending on the type of catalysts used, and for a time sufficient to obtain the desired product(s), generally for about 5 minutes to about 1440 minutes. For economical operation, the reaction time is usually maintained between 20 minutes to 10 hours. For most homogeneous catalysts, such as shown in Formula 1 to 3 (First and Second generation Grubbs Catalysts and the Hoveyda-Grubbs Catalyst) or activated $WCl_6$ or $MoCl_6$ catalysts, the reaction is advantageously conducted between room temperature to 150° C. For solid supported catalysts, such as activated $Re_2O_7/Al_2O_3$, the reaction can be carried out at higher temperature range, between room temperature to 300° C., usually 50° C. to 250° C. The amount of the catalyst used for the metathesis can range from 10 ppm to 5 wt % of the reaction medium. For an economical process, it is advantageous to conduct the reaction with lowest possible catalyst content, especially when using the more expensive Formulas 1 to 3 catalysts. In order to obtain the highest catalyst efficiency, it is advantageous to use triglycerides and alkenes of highest purity, with minimum amount of dissolved oxygen, water, sulfur- or nitrogen-containing impurity. This can be accomplished in any known manner e.g., by passing the feed through activated molecular sieve, purging with pure nitrogen gas, or subjecting the feed to vacuum to remove water, oxygen, etc. All metathesis reactions should be carried out under inert nitrogen or argon atmosphere. The metathesis can also be carried out using solvents. Exemplary solvents include hexanes, heptane, toluene, benzene, xylene, methylene chloride. The reaction can be carried out in batch mode or in continuous stir tank mode. The reaction time ranges from 10 minutes to 100 hours, depending on the desired catalyst concentration, final conversion, temperature, etc. The conversion of the metathesis reaction can range from 10% to 100%. Usually it is advantageous to have high conversion of triglycerides (>70%). Alternatively, the conversion may be deliberately maintained at partial conversion, such as 40-70% to maximize process economics.

Polymerization of Olefins to Synthetic Hydrocarbon Fluids

For purposes of this first embodiment, oligomeric synthetic hydrocarbon fluids (also referred to herein as "synthetic hydrocarbon fluids") include PAOs, poly internal-olefins, and copolymers of alpha-olefins, such as linear alpha-olefins, and internal olefins, and mixtures thereof. Particularly, the LAOs and internal olefins, which are obtained through catalytic metathesis of natural oils and an alkene are polymerized to produce PAOs.

The polymerization process of LAOs and internal olefins into synthetic hydrocarbon fluids is conducted in the presence of suitable catalysts, such as Friedel-Crafts catalysts including $AlCl_3$, $BF_3$, or promoted $AlCl_3$, $BF_3$, or Ziegler catalysts in the presence of $H_2$, or metallocene catalyst system or systems promoted by a non-coordinating anion or methylaluminoxane or activated chromium oxide on silica gel catalyst. When Friedel-Crafts catalysts such as $AlCl_3$, $BF_3$ or promoted $AlCl_3$ or $BF_3$ are used for the polymerization process, both LAO and internal olefins can be co-polymerized to give polymeric synthetic hydrocarbon fluids. When other catalysts, such as Ziegler catalysts, $CrO/SiO_2$ catalyst, or metallocene catalyst are used for the polymerization process, only LAO will be polymerized to give poly-alpha-olefins (PAO). The internal olefins will not be incorporated into the polymer.

When the polymerization is completed, the polymers or oligomers can be separated by typical aqueous work up procedures. In the aqueous work up procedures, the reaction mixture is quenched with dilute sodium hydroxide solution to deactivate and decompose the catalyst components. All metal components can be washed out using dilute acid (such as HCl, 5% in water) or dilute base (such as NaOH 5% in water), followed by washing with water to remove any residual salts. The organic layer can be then dried by a drying agent or dried by heat and vacuum. The polymer fraction can be isolated by any suitable procedure, e.g., by distillation under vacuum to remove light solvent or other low boiling fraction. In many cases, when polymerization is carried out in the absence of $H_2$ gas, the residual polymer has relatively high bromine number, usually greater than 1 or 2. In such case, a standard hydrogenation step is necessary to reduce the bromine number to below 5, below 4, below 3, below 2 or below 1. This hydrogenation step can be carried out using supported nickel or palladium catalyst at 200° C. with $H_2$ pressure of 300-800 psi for 1 to 10 hours. Typical hydrogenation conditions can be found in many PAO synthesis publications, including patents. When $H_2$ is used in polymerization step and the residual polymer has low bromine number, typically below 3 or below 2, the polymer can be used as is in a lube formulation and no separate hydrogenation step is needed. Or alternatively, if the catalyst concentration is very low (about below 1000 ppm), the catalyst can be removed by adding a solid sorbent, followed by filtration. This method of catalyst removal is very convenient and advantageous for process economics.

The unreacted or partially reacted triglycerides can be recycled, or separated for use as polar synthetic lubricant base stock or as plasticizers, or used as starting material for biodiesel production.

Optionally, the LAO and internal olefins can be separated by fractionation, distillation or other appropriate separation method, such as sorption method. The LAO can then be separately polymerized by any one of the above catalysts. The internal olefins can be polymerized only by the Friedel-Crafts catalyst. Or alternatively, the LAO and internal olefins can be combined in specific proportions as the feed for polymerization by a Friedel-Crafts catalyst.

Polymerization processes of olefins using the catalysts stated above are known in the art: see U.S. Pat. Nos. 3,997,621; 6,949,688; 3,833,678; 6,410,812; 3,997,621; 6,949,688; 3,149,178; 3,382,291; 3,742,082; 3,780,128; 4,172,855; 4,956,122; WO 2007/111,776; and WO 2007/011,462, all of which are incorporated by reference herein. U.S. Pat. Nos. 4,827,064 and 4,827,073 describe the LAO oligomerization or polymerization by $CrO/SiO_3$ (chromium oxide supported on silica) catalyst. U.S. Pat. No. 6,949,688 describes a process for polymerization of olefins in the presence of a promoted $BF_3$ catalyst. Polymerization of olefin feed may be conducted in the presence of $BF_3$ and at least two different co-catalysts which are (i) alcohols and (ii) alkyl acetates. At least one co-catalyst is selected from the class of alcohols, i.e., compounds having one hydroxyl functional group, such as, $C_1$-$C_{10}$ alcohols, or $C_1$-$C_6$ alcohols, and at least one co-catalyst is selected from alkyl acetates, such as $C_1$-$C_{10}$ alkyl acetates, or $C_1$-$C_6$ alkyl acetates. This may be followed by hydrogenation of at least a portion of residual unsaturation to produce a lubricant. The ratio of the alcohols to alkyl acetates ranges from about 0.2 to 15, such as 0.5 to 7. U.S. Pat. Nos. 4,827,064; 4,827,073 and 6,949,688 are incorporated herein by reference.

Another example is U.S. Pat. No. 6,410,812, which discloses a method for separating at least a part of the $BF_3$ present in a mixture comprised of $BF_3$ and $C_1$-$C_{10}$ alcohols, wherein excess $BF_3$ is present in the mixture that is used to form a complex of $BF_3$ and alcohol. The method comprises (a) reducing the pressure of the mixture sufficiently to cause the separation of $BF_3$ vapor from a liquid organic phase which includes $BF_3$/alcohol complex; (b) recovering the $BF_3$ vapor separately from the liquid organic phase; and (c) mixing the $BF_3$ vapor from step (b) with fresh alcohol using countercurrent flow to form additional $BF_3$/alcohol complex. This method is particularly useful in a process which to utilizes the $BF_3$/alcohol complex as a catalyst in a reaction zone for the oligomerization of alpha-olefins.

U.S. Pat. No. 6,410,812 also discloses a process scheme for the oligomerization of an alpha-olefin or alpha-olefins in the presence of $BF_3$ catalyst which comprises (a) contacting in an oligomerization zone an alpha-olefin or alpha-olefins feed with a catalytic mixture comprising an effective catalytic amount of a catalyst complex consisting of $BF_3$ and a protic promoter under conditions and for a time sufficient to oligomerize the alpha-olefins in the feed whereby a liquid organic mixture is formed comprising PAOs and the catalytic mixture; (b) recovering the liquid organic mixture from the oligomerization zone; (c) reducing the pressure of the liquid organic mixture recovered in step (b) sufficiently to separately recover a gas comprising at least a portion of the $BF_3$ present in the catalytic mixture and a liquid product stream comprising the PAO product and residual catalyst complex; (d) mixing the gaseous $BF_3$ recovered from step (c) with fresh protic promoter to form fresh catalyst and promoter mixture; (e) introducing the fresh catalyst complex from step (d) into the oligomerization zone of step (a); and (f) recovering the PAO product from the liquid product stream of step (c).

The protic promoter forms a catalyst complex with the $BF_3$, and the complex serves as a catalyst for the oligomerization of alpha-olefins. The protic promoter will usually be a $C_1$-$C_{10}$ alcohol. The catalytic mixture comprising the $BF_3$/alcohol complex usually also contains excess $BF_3$, which is adsorbed in the mixture. It is primarily the excess $BF_3$, which is recovered by the method described in U.S. Pat. No. 6,410,812.

Another example is PCT Patent Publication No. WO 2007/111,776, which describes a process for oligomerizing mixtures of 1-hexene/1-dodecene/1-tetradecene, optionally with 1-octene or 1-decene in the presence of a catalyst comprising an aluminum halide, complex with water, such as aluminum trichloride—water complex having 0.5 moles of water per mole of aluminum chloride. This reaction may be batch, semi-batch or continuous, in a single or multi-stage reactor.

Yet another example is PCT Patent Publication No. WO 2007/011,462, which describes polymerization process of a mixture of LAOs, which can be selected from $C_3$ to $C_{30}$ linear alpha olefins in the presence of an activated metallocene catalyst. The activated metallocene catalyst can include simple metallocenes, substituted metallocenes or bridged metallocene catalysts activated or promoted by, for instance, a non-coordinating anion or methylaluminoxane.

For purposes of all embodiments of this disclosure and the claims, a non-coordinating anion is defined to mean an anion which either does not coordinate to the catalyst metal cation or that coordinates only weakly to the metal cation. A non-coordinating anion coordinates weakly enough that a neutral Lewis base, such as an olefinically or acetylenically unsaturated monomer, can displace it from the catalyst center. Any metal or metalloid that can form a compatible, weakly coordinating complex with the catalyst metal cation may be used as or be contained in the noncoordinating anion. Suitable metals include, but are not limited to, aluminum, gold, and platinum. Suitable metalloids include, but are not limited to, boron, aluminum, phosphorus, and silicon. A subclass of non-coordinating anions comprises stoichiometric activators, which can be either neutral or ionic. The terms ionic activator, and stoichiometric ionic activator can be used interchangeably. Likewise, the terms neutral stoichiometric activator and Lewis acid activator can be used interchangeably.

For the purposes of all embodiments of this disclosure and the claims, any one of the catalysts and processes described in the patents and patent publications, identified in the preceding paragraphs of this section, and in any relevant patents and patent publications described elsewhere in this disclosure, which may be suitable for the production of synthetic hydrocarbon fluids, as discussed herein may be used in the processes described herein.

The synthetic hydrocarbon fluids can be used as lubricant base stocks.

The PAOs or synthetic hydrocarbon fluids prepared as described herein, particularly those of moderate to high viscosity (such as those with a $Kv_{100}$ of greater than about 2 cSt, such as 3 to 3000, or about 3 to about 3000 cSt) are especially suitable for use in the formulation of high performance automotive engine oils, general industrial lubricants, grease, various types of automotive or industrial gears oils, aviation lubricants, hydraulic fluids or lubricants, heat transfer fluids, etc. These PAOs, prepared from the LAOs, synthesized from metathesis chemistry are substantially not distinguishable from the commercial PAO produced from commercial LAO made from ethylene growth reaction known in the art. The synthetic hydrocarbon fluids made by our processes described herein, polymerized from the mixture of the LAO and the internal olefins or from the internal olefins are also very similar in properties to the commercial PAO fluid. This is quite unexpected. The PAO or synthetic hydrocarbon fluids obtained in our processes described in this embodiment have viscosity greater than about 1.5 cS. Most commonly, the PAO or synthetic hydrocarbon fluids obtained by the polymerization of LAO and the internal olefins or from internal olefins from the self-metathesis, have viscosity of about 3 cS to about 1000 cS. The fluids usually have viscosity index (VI) of greater than about 80, greater than about 100, greater than about 110, greater than about 120, greater than about 130, greater than about 140, or greater than about 150, or ranging from 90 to 350 or about 90 to about 350. These fluids usually have very low pour points, such as less than 0° C., ranging from about −20 to about −75° C. or less than about −75° C. to about 0° C. depending on fluid viscosity. VI and pour points are generally a function of viscosity or molecular size. For one class of fluids, lower viscosity fluids have lower pour point and lower VI. Higher viscosity fluids have higher pour points and higher VI. The fluids made in this process have similar or better pour points than fluids made from LAO of comparable carbon length made from ethylene growth reaction or other conventional LAO synthesis process. Fluids having viscosity of about 3 to about 6 cs can be advantageously used as high performance automotive crank case lubricants. High viscosity fluids can be used as viscosity booster, as high performance industrial lubricant, as grease or gear oil formulation. The PAO's or synthetic hydrocarbon fluids prepared as described herein can be used by themselves as base stocks or by blending 0.1 up to 95 wt % of the PAOs or synthetic hydrocarbon fluids with other fluids, such as Group I, II, Group II+, Group III, Group III+ base stocks or lube base stocks derived from hydroisomerization of wax fractions from Fischer-Tropsch hydrocarbon synthesis from $CO/H_2$ syn gas (GTL lube base stock), or other Group IV or Group V or Group VI base stocks. General description of these base stocks can be found in Chapter 18 and 19 of the book, "Synthetics, Mineral Oils, and Bio-Based Lubricants, Chemistry and Technology", ed. L. R. Rudnick, published in 2006 by CRC Press, Taylor & Francis Group of Boca Raton, Fla. 22487-2742, incorporated herein by reference. These blend stocks, when combined with additives known in the industry, are used to formulate into full synthetic lubricants, partial synthetics, or used as special additive components with other base stocks.

In an embodiment, a novel lubricant of the present disclosure comprises a lubricant blend composition which includes the PAOs produced as described herein, together with one or more other base stocks (which also may be referred to as "second base stock"), including Group I to Group VI base stocks, a lube base stock produced from gas-to-liquid conversion process (GTL lube) or any combination thereof. Suitable combinations of such other base stocks include, without limitation, Group III and Group IV base stocks, Group IV and Group V base stocks, Group II and Group III base stocks, Group III and Group V base stocks, Group I and Group II base stocks, Group I and Group III base stocks, and at least one of Groups I-VI base stocks and the GTL lube. The lubricant blend composition comprises about 0.1 to about 90 wt % of the poly-alpha olefins of this disclosure, and about 10 to about 99.9% wt % of the second base stock. The lubricant blend composition has unique lubrication properties, including $K_{v100}$ of about 2 cSt to about 300 cSt, $K_{v40}$ of about 4 cSt to about 6,000 cSt, VI of about 100 to about 300, such as about 120 or greater than about 120, or greater than about 130, or greater than about 140, or greater than about 150. The lubricant blend composition has pour point of less than about 0° C., such as less than about −10° C., less than about −20° C., less than about −30° C., or less than about −40° C. The Noack volatility of the lubricant blend composition is less than about 5 wt %, such as less than about 8%, less than about 10%, less than about 12%, less than about 15%, or less than about 18%. In an embodiment, the second base stock has Kv at 100° C. of 3 cS to 200 cS or about 3 to 100 cS, or about 4 to 20 cS, as available in Gr I, II, III, IV (PAO) base stocks or GTL lubes. Sometimes, it is desirable to blend with lowest viscosity base stock a highest possible viscosity fluid to achieve maximum increase in VI and/or maximum decrease in pour point for the final blend product. In special applications when very high viscosity is needed, such as in heavy gear lubricants or cylinder oils, it is beneficial to blend a high viscosity PAOs described herein with another oil of 40 to 3000 cS (measured at 100° C.), such as conventional heavy neutral base stocks or bright stock or PAO (such as SpectraSyn™ 20, SpectraSyn™ 40, or SpectraSyn™ 100, or SpectraSyn Ultra™ 150, or SpectraSyn Ultra™ 300, or SpectraSyn Ultra™ 1000) to give optimized finished lubricants. In addition, additives of one or more of: thickeners, VI improvers, antioxidants, anti-wear additives, detergent/dispersant/inhibitor (DDI) packages, and/or anti-rust additives may be added.

In one embodiment, the PAOs produced herein are combined with one or more of dispersants, detergents, friction modifiers, traction improving additives, demulsifiers, defoamants, chromophores (dyes), and/or haze inhibitors. These fully formulated lubricants can be used in automotive crank case oil (engine oil), industrial oil, grease, hydraulic, gear oils, heat transfer fluids or gas turbine engine oils. These are non-limiting examples of additives used in finished lubricant formulations. Additional information on the use of the PAOs and Gr. I to VI and GTL base stocks of this disclosure in the formulations of full synthetic, semi-synthetic or part synthetic lubricant or functional fluids can be found in "Synthetic Lubricants, Mineral Oils and Bio-Based Lubricants", Ed. by L. R. Rudnick, CRC Press, Taylor & Francis Group, 2006, incorporated herein by reference. Additional information on GTL lube can be found in U.S. Pat. Nos. 6,420,618 and 7,132,042, both being incorporated herein by reference. Additional information on additives used in product formulation can be found in "Lubricants and Lubrications, Ed. By T. Mang and W. Dresel, by Wiley-VCH GmbH, Weinheim 2001, incorporated herein by reference.

Figure 1:
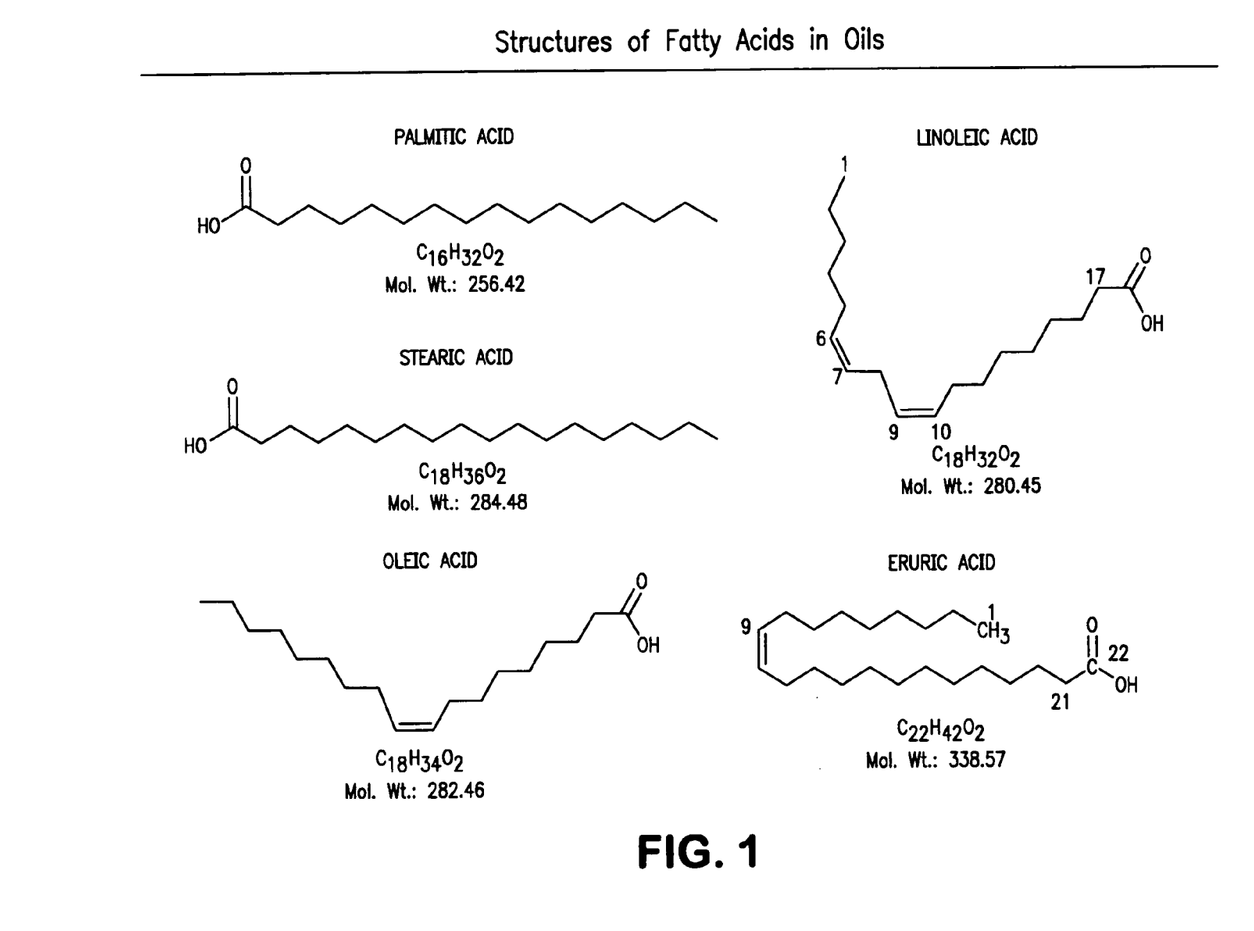
FIG. 1 shows chemical structures of some fatty acids in oils.
Figure 2:
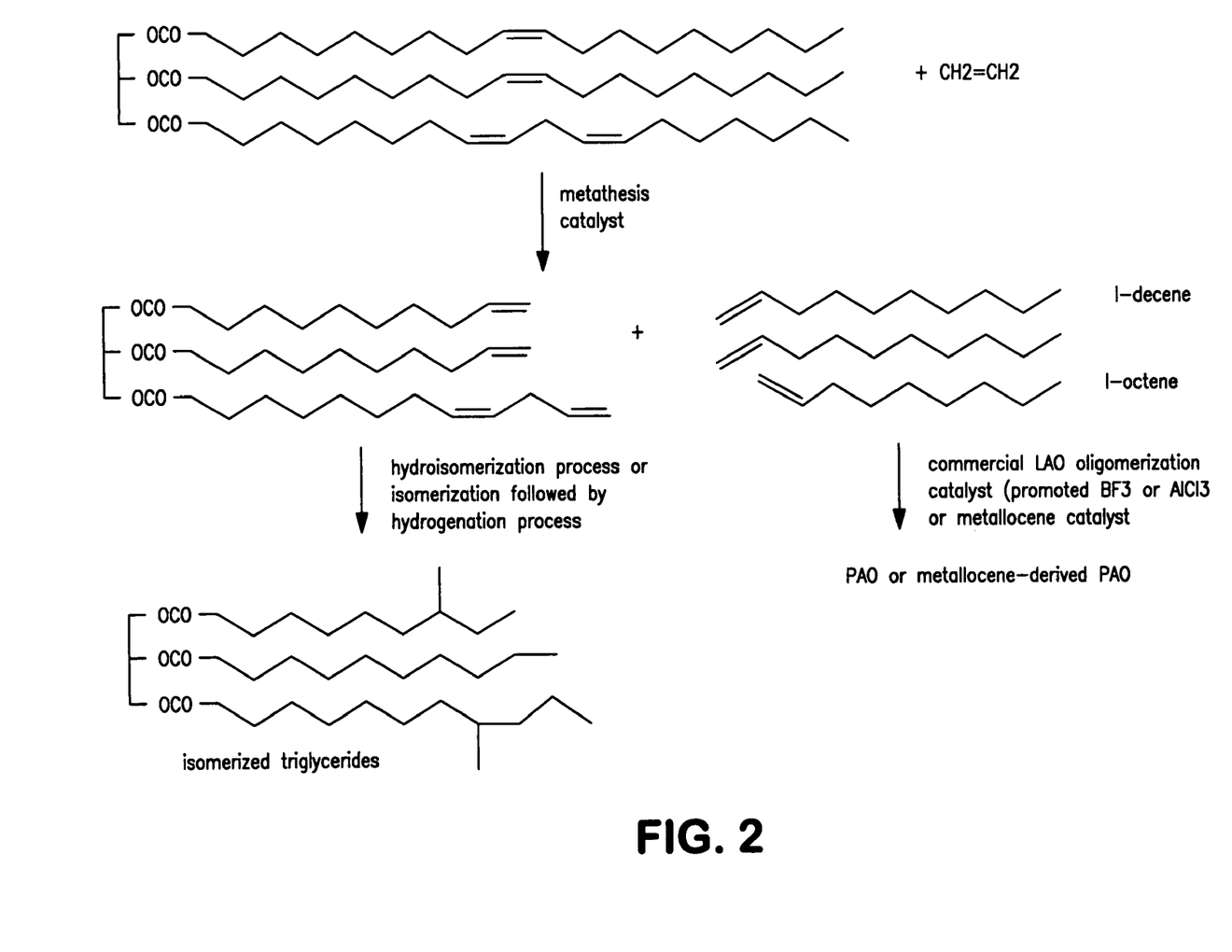
FIG. 2 shows schematically an integrated process (of the first embodiment, scheme A) of producing synthetic hydrocarbon fluids, plasticizers and synthetic polar lubricant base stocks from renewable feedstocks.

Conversion of Reduced Chain Length Triglycerides to Polar Synthetic Lubricant Base Stocks or Plasticizers For purposes of this first embodiment, the method of converting the reduced chain length triglycerides to synthetic ester lubricant base stocks (also referred to herein as polar synthetic lubricant base stocks) and plasticizers comprises isomerization, followed by hydrogenation, or by hydroisomerization process of these triglycerides. See scheme A, FIG. 2. Such processes of isomerization, followed by hydroisomerization are known, e.g., see U.S. Pat. Nos. 7,022,784 and 7,456,329, incorporated herein by reference. The processes described in these patents can be readily adapted for the production of the synthetic ester lubricant stocks and plasticizers of this disclosure. Furthermore, European Patent Publication No. 508,418, incorporated herein by reference, discloses the use of unisomerized triglycerides as lube base stocks. The synthetic ester lubricant base stocks may comprise glycerol esters of fully saturated $C_6$ to $C_{14}$ fatty acids with linear or branched carbon chains or with a mixture of linear and branched carbon chains. The polar synthetic lubricant base stock or stocks has (have) 100° C. Kv of 2 cS to 20 cS, VI greater than 80 and Noack volatility of 20% or less and better oxidative stability than the natural oils or the fatty acid derivatives from planst oils or animal fats/oils, e.g., mono-esters. The plasticizers comprise medium chain length triglycerides produced by methathesis.

The plasticizers produced through this integrated process contain medium chain length triglycerides. Medium chain length tryglycerides means a mixture of: (i) triglycerides made with medium chain length fatty acids ($C_7$-$C_{12}$ acids or $C_6$-$C_{17}$ acids); (ii) triglycerides made with short chain length fatty acids ($C_4$-$C_8$); and (iii) and triglycerides made with long chain length fatty acids ($C_8$-$C_{12}$). The average chain length of the medium chain length triglycerides is $C_8$-$C_{12}$. The use of the medium chain length triglycerides results in a plasticizer with improved compatibility as a plasticizer relative to naturally occurring long chain length triglycerides. The plasticizer or plasticizers based on the medium chain length triglycerides are advantageous as plasticizers over triglycerides with short alkyl chains which have high volatility and are lost due to volatilization during processing. In addition, it should be noted that the triglyceride based plasticizers are non-phthalate plasticizers and are expected to have low toxicity. The plasticizers resulting from this process are expected to have good low temperature properties, e.g., pour point.

Variations and modifications of the description of the first embodiment are contemplated. For example, the ethylene used in the metathesis reaction can be derived from the dehydration of bio-ethanol fuel—an all-renewable process scheme. Alternatively, the ethylene may be derived from a conventional petroleum feedstock As the feed stock material for the initial metathesis step of the integrated process, bio-diesel may be used, which is mostly methyl ester of unsaturated fatty acids, together with or as a substitute for seed oil(s). The product from the bio-diesel is expected to be LAOs and methyl ester of unsaturated acids. The LAOs can be used as a feed for PAOs synthesis. The methyl ester can be used as chemical feed stocks.

II. Second Embodiment

The starting feed material for this embodiment is at least one natural oil, as defined above, which includes triglyceride esters. As also stated above, the term "renewable feedstock" is synonymous with the term "natural oil" which includes plant oils and vegetable oils and animal oils. The plant or vegetable oil may also be referred to herein as "seed oil". Plant oils may include corn oil, sugar cane oil, canola oil, sunflower oil, rapeseed oil, mustard oil, olive oil, peanut oil, soybean oil, cottonseed oil, palm kernel oil, palm oil, coconut oil, rice bran oil, linseed oil, fax seed oil, sesame oil, or any oil derived from plant or vegetable material, etc. Animal oil, animal fats or animal lard can also be used as a starting material. Examples include the glycerides derived from beef fats, pork fat or lard, chicken fats, goal or sheep fats, whale fats, suet fats, tallow fats, or any fats or oils derived from animal parts. All such oils, including animal oils, are the same as described above in the first embodiment.

An advantageous starting natural oil or oils for the process of this embodiment should contain a relatively high amount of components having a single unsaturated double bond in the fatty acid (e.g., mono-unsaturated fatty acids). Examples of the mono-unsaturated fatty acids include cis-5-dodecenoic acid, myristoleic acid (cis-9-tetradecenoic acid, C14:1), palmitoleic (cis-9-hexadecenoic acid, C16:1), oleic acid (cis-9-octadecenoic acid, C18:1), gadoleic acid (cis-1'-eicosenoic acid C20:1), eruric acid (cis-13-docosenoic acid C22:1). Although most natural occurring oils contain cis-isomers of fatty acids, their trans-analogs occurring naturally or via isomerization process during treatment, such as hydrogenation, can also be used. Other odd carbon number mono-unsaturated acids, cis or trans form, although rare in natural products, can also be used. Generally, oils rich in the cis-form of the mono-unsaturated acids are most abundant in natural oils especially plant-based oils, and are advantageous feeds. For example, canola oil, some rapeseed oil or some mustard oil includes 57%-60% monounsaturated fat, olive oil is about 75% monounsaturated fat while tea seed oil commonly includes over 80% monounsaturated fat. Oils which contain some di-unsaturated fatty acid moiety can also be used for this embodiment. They can be converted in the metathesis reaction to mono-alpha-olefins, linear alpha-olefins, internal olefins or di-olefins and reduced chain triglycerides by the process described herein. The di-olefins can be separated from the mono-alpha-olefins. In this embodiment, it may be advantageous to produce low amount of di-olefins from the metathesis step, at least for the lubricant application.

When choosing a feed from animal fats, it is advantageous to choose one that contains higher percentages of mono-unsaturated fatty acids and lower amount of fully saturated fatty acid or multi-unsaturated fatty acid. Although is animal fats, lard and oils can be used for this process, the yields to LAO maybe lower than from plant-based oils because most animal fats, such as beef fat, pork fat, or suet, etc. contain higher amount of saturated fats than plant-based oils.

Freshly produced plant-based oils or animal-based fats/oils can be used as starting material. Used or treated plant oil or animal fats/oils can also be used as starting material. The used plant oils can be obtained from food preparation, cooking, or other processes that recover or recycle used plant oils or animal fats/oils. Many of the used plant oils may contain partially hydrogenated plant oils. Thus, they may contain the glycerides of the naturally occurring acids (mostly cis-acids) and also some glycerides of the corresponding isomerized trans-acids. These trans-acids of mono- or di-unsaturated acids are also suitable as feed for processes of this embodiment. In order to optimize product yields, the impurities in the used plant oils, such as water, decomposed products, sludges, carry-over component from the foods, etc. should be removed by pretreatments, known in the art, such as settlement and decantation, clarification, passing through drying column and similar procedures.

The rapeseed oils, canola oils, mustard oils or olive oils usually include triglycerides of long-chain fatty acid esters. In particular, suitable seed oils for this embodiment may include oils which have a significant amount of the glycerides of mono-unsaturated acids, such as myristoleic acid, palmitoleic, oleic, linoleic, gadoleic, behenic, eruric, and lauroleic acids, etc. These fatty acids are most suitable in conversion into desirable $C_5$ to $C_{14}$ linear alpha-olefins.

Soybean oil contains a relatively high amount of di-unsaturation in the form of linolenic acid in the fatty acid moiety, as discussed above in the first embodiment. It can be used as a starting material for the process to produce alpha-olefins. After metathesis of the soybean oil with ethylene, the alpha-olefin fraction may contain a mixture of 1-octene, 1-decene and 1,3- or 1,4-di-olefins of $C_{11}$. These olefins can be used as a starting material for synthetic hydrocarbon fluids synthesis. There are many reports of utilizing a modified soybean plant to produce soybean oil [e.g., Genetic enhancement of soybean oil for industrial uses: prospects and challenges, by Edgar B. Cahoon, USDA Research Service, AgBioForum 6 (1&2): 11-13. @2003 AgBioForum, and references therein, incorporated herein by reference,] with very high amount of oleic acid moiety, as high as 85% oleic acid content, vs. 25% oleic acid content made from traditional, i.e., naturally occurring, soybean plant. Such modified soybean plant with high oleic content is advantageous for the process of this embodiment, described herein.

Reacting Natural Oils or Their Derivatives with Lower Alkene in the Presence of Metathesis Catalyst As discussed in the first embodiment, cross-metathesis and co-etathesis are synonymous, and include the metathesis reaction of triglycerides having long-chain fatty acid esters (e.g., $C_{16}$-$C_{22}$) with an alkene or a mixture of alkenes. Examples of the alkenes include ethylene, propylene, 1-butene, cis- or trans-2-butene, 1-pentene, cis- or trans-2-pentene, 3-pentenes, 1-hexene, 2-hexene, a mixture of these olefins, such as mixed butenes containing 1- and 2-butenes, n-pentenes, n-hexenes, etc. The alkene fraction may contain other inert components. For example, C4 stream from a refinery containing 1-, 2- and iso-butenes and n-butane and/or isobutene can be used. Other mixed streams containing mixtures of pentenes, and pentanes can also be used. Generally, when ethylene is used as the co-metathesis reagent, it favors the formation of LAO. When other alkenes (which may also be referred to herein as "olefin") are used, they usually produce a mixture of LAO and internal olefins. When internal olefins are used to co-metathesis with the triglycerides having long chain unsaturated fatty acids, the product olefins are mostly internal olefins. Usually, advantageous olefins for co-metathesis with a feed comprising natural oils (which include triglyceride esters) are lower olefins, such as ethylene, propylene or butenes. Ethylene is advantageous to generate LAO with highest catalyst reactivity, productivity and most desirable product quality. Propylene and butenes are also desirable olefins for co-metathesis for slightly different reasons. Propylene and butenes sometimes are more desirable for co-metathesis with the natural oils because they are readily condensable gases and can be dissolved in or be in close contact with the feed during reaction. Thus, higher concentration of propylene or butenes can be maintained in the metathesis mixture, to increase the yield of cross- or co-metathesis product between olefins and glycerides; and reduce the amount of self-metathesis of the glycerides, when it is more desirable to do so.

Generally higher alkene concentration in the reaction medium favors cross- or co-metathesis. When ethylene is used for co-metathesis, it is more desirable to run the reaction at higher pressure, and lower temperature and high stirring rate to maximize the ethylene concentration in the reaction medium. When ethylene is used for co-metathesis with natural oils (containing triglycerides), substantially constant ethylene pressure is maintained of greater than 1 atmosphere, greater than 100 psi, greater than 200 psi, greater than 500 psi, greater than 750, greater than 1000 psi, or greater than 1500 psi. Usually the range of about 0 to about 3000 psi, or 200 psi to 1000 psi can be used. If appropriate, propylene, butenes and pentenes are advantageous for co-metathesis with glycerides. Usually the amount of the alkenes used is at least in equal molar ratio to the amount of unsaturation or double bonds in the glycerides. Usually, it is advantageous to have the molar ratio of alkenes to unsaturated double bonds of greater than 1.5, or greater than 2, or greater than 3, or greater than 5. When excess alkenes are used in the co-metathesis, the un-reacted alkenes can be recycled and reused. Higher amount of alkenes in the reaction medium promotes co-metathesis. Lower amount of alkenes allows more self-metathesis of the triglyceride esters. Too high amount of olefins reduces reactor efficiency, requires large reactor, more catalyst, and may reduce overall process efficiency. Therefore, there is an optimum alkene concentration, which depends on the desirable degree of co-metathesis vs. self-metathesis, the process economics and product selectivity, etc. One skilled in the art may determine the appropriate alkene concentration without more than routine experimentation. Sometimes, it is also desirable to conduct the co-metathesis reaction to convert only part of the triglycerides or the fatty acid. In this case the molar ratio of olefin to unsaturation can be below 1, such as 0.9 or 0.7. Without being bound by any operability theory, it is believed that when an effective amount of an alkene is not present to affect a significant amount of a cross-metathesis reaction, the triglycerides having long-chain fatty acid esters may undergo a self-metathesis reaction and produce internal olefins. An excess of an alkene can force a substantially pure cross-metathesis reaction and suppress self-metathesis of the triglyceride esters.

Triglycerides having long-chain fatty acid esters (e.g. $C_{16}$-$C_{22}$) can be shortened via a metathesis reaction with an alkene (e.g., ethylene, propylene, butenes, etc.) in the presence of a metathesis catalyst (e.g., Grubbs catalyst) to produce a desired mix of components: (i) LAOs (e.g., $C_6$-$C_{12}$ alpha-olefins), in particular, a significant amount of 1-decene, which is in great demand; (ii) some amount of internal olefins (e.g., $C_{16}$-$C_{22}$ internal olefins, in particular, 9-octadecene); (iii) small amount of di-olefins (e.g., 1,4-octadiene, 1,4-decadiene and 1,4-dodecadiene); (iv) 1-hexene, 1-octene; and (v) reduced chain length triglycerides (e.g., $C_8$-$C_{14}$). The internal olefins that are produced in the metathesis reaction have the double bond placed substantially in the center of the carbon chain.

Metathesis Catalysts

The metathesis catalysts suitable for this embodiment are the same as used in the first embodiment.

The metathesis reaction of this embodiment is conducted in substantially the same manner as, and at substantially the same conditions of temperature, olefin partial pressure or content and all other conditions as the metathesis reaction of the first embodiment.

Figure 3:
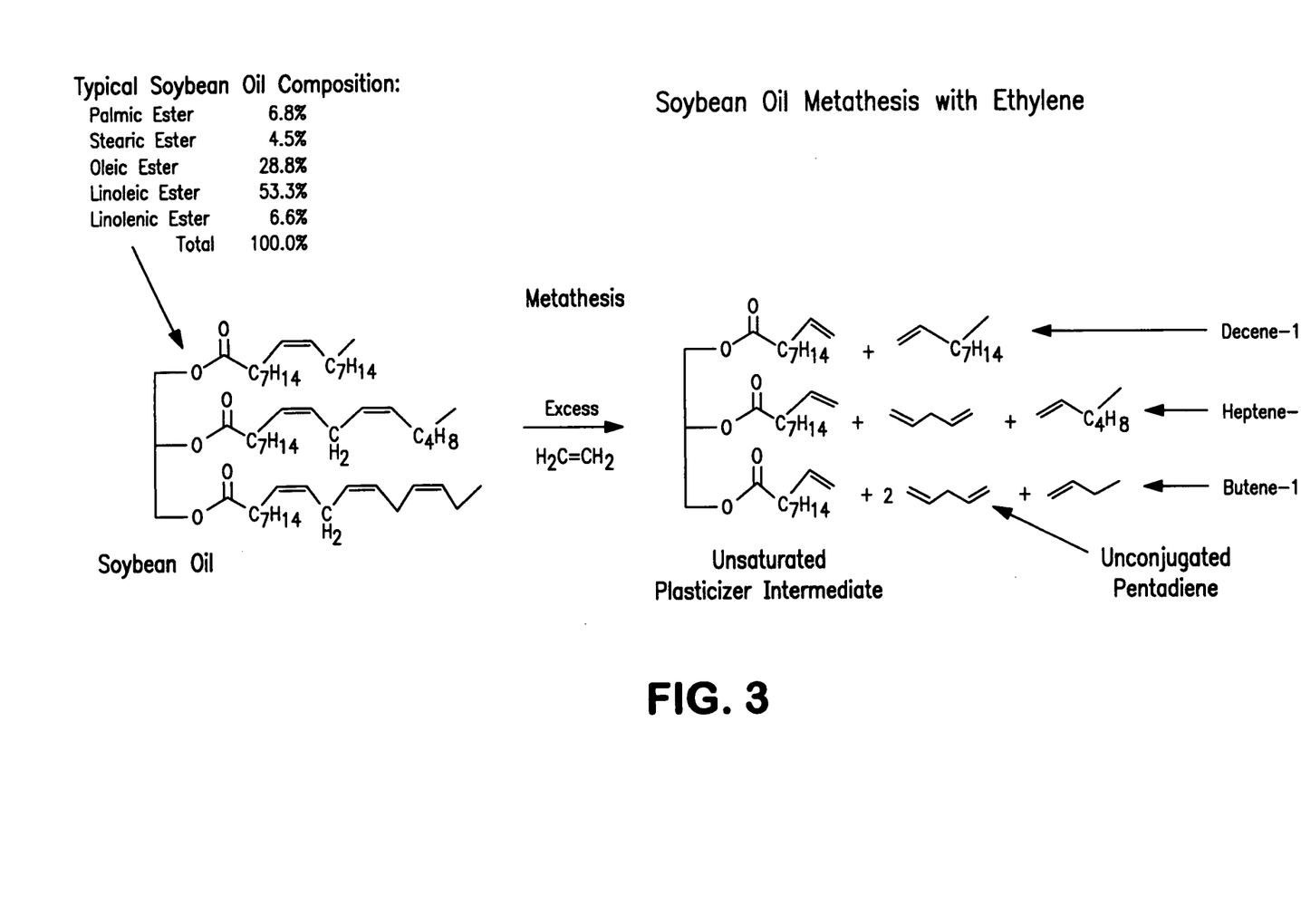
FIG. 3 shows schematically a cross-metathesis reaction (of the second embodiment), of soybean oil and ethylene to produce olefins, such as 1-decene, 1-heptene and 1-butene as well as unsaturated plasticizer intermediate and unconjugated pentadienes.

This embodiment includes the production of non-phthalate plasticizers comprising the preparation of a triglyceride structure directly from vegetable oils, such as soybean oil, by first metathesizing these vegetable oils with a lower alkene, as described in connection with the first embodiment in the presence of a suitable metathesis catalyst (as described in the first embodiment), to produce a triglyceride structure with unsaturated $C_9$ ester groups containing a double bond at the terminal position of the three alkyl chains of the triglyceride. (This structure is also referred to herein as "$C_9$ tryglyceride product" or "metathesized tryglyceride"). Examples of the lower alkenes include ethylene, propylene, 1-butene, cis- or trans-2-butene, 1-pentene, cis- or trans-2-pentene, 3-pentenes, 1-hexene, 2-hexene, mixture of these olefins, such as mixed butenes containing 1- and 2-butenes, n-pentenes, n-hexenes, etc. If soybean oil is used as the starting material, this metathesis reaction is expected to also simultaneously coproduce LAOs, such as butene-1, heptene-1, decene-1, as well as diolefins, such as, unconjugated pentadiene. This metathesis chemistry is schematically shown in FIG. 3. The butene-1, and heptene-1 alpha olefins produced are commercially useful as comonomers in polyethylene polymerization, while the decene-1 is potentially useful as a raw material for producing PAOs for synthetic lubricants and/or lubricants base stocks and plasticizers. The unconjugated pentadiene is useful as a polymer crosslinking agent, or in the production of resin adhesives.

Oxidation, and Optionally, Carbonation of Unsaturated $C_9$ Triglycerides

The unsaturated $C_9$ triglyceride product of the metathesis reaction has alkyl chains that are expected to be slightly too long to allow full compatibility with polyvinyl chloride (PVC) (see "Structural Expressions of Long-Chain Esters on Their Plasticising Behavior in Poly(vinyl chloride)", H. K. Shoba and K. Kishore, Macromolecules, 1992, 25, 6765-6769.) As a result, additional polarity may need to be incorporated into the $C_9$ triglyceride product. This can be accomplished by epoxidizing the terminal double bonds via oxidation (e.g., with hydrogen peroxide or ozone) to form an epoxidized triglyceride structure. Similar reactions are widely practiced commercially on soybean oil to form epoxidized soybean oil (ESO). (For example, see Ullmann's Encyclopedia of Industrial Chemistry, "Epoxides", G. Sienel, R. Rieth and K. Rowbottom, John Wiley and Sons, 2008 edition, incorporated herein by reference). Once formed, the epoxidized triglyceride can then be used as a plasticizer, or can be further modified to form carbonates from the epoxide groups via a reaction with carbon dioxide. Carbonates are produced in high yield by the reaction of an epoxide with carbon dioxide in the presence of tetrabutylammonium bromide as a catalyst (e.g. see B. Tamami, S. Sohn, and G. L. Wilkes, J. Appl. Poly. Sci., (2004), 92(2), 883, incorporated herein by reference). These subsequent functionalization steps to form the epoxides and carbonates of the unsaturated $C_9$ triglyceride are shown in FIG. 4.

For purposes of this second embodiment, epoxidized triglyceride plasticizers and carbonated triglyceride plasticizers, each individually or together, may be referred to as the "inventive material" or "inventive materials."

Triglyceride alkyl groups may need to be only partially epoxidized and/or carbonated, because the polarity of the plasticizers needs to be balanced to achieve compatibility with PVC. In such case, it may be necessary to partially hydrogenate double bonds in the metathesized triglycerides prior to oxidation to the epoxide triglyceride plasticizers. Because some of the vegetable oil triglyceride alkyl groups are saturated (e.g., approximately 7% of such groups in soybean oil are palmic ester chains), some longer chain triglycerides will also be a co-product of the above metathesis reaction. These saturated vegetable oil triglyceride alkyl groups will typically be less than 10% of the total vegetable oils, and can be converted to glycerol and fatty acids by transesterification with methanol. The palmic acid methyl esters can be used as biodiesel, while the $C_9$ fatty acids can be used for other purposes, such as soaps and detergents.

Figure 4:
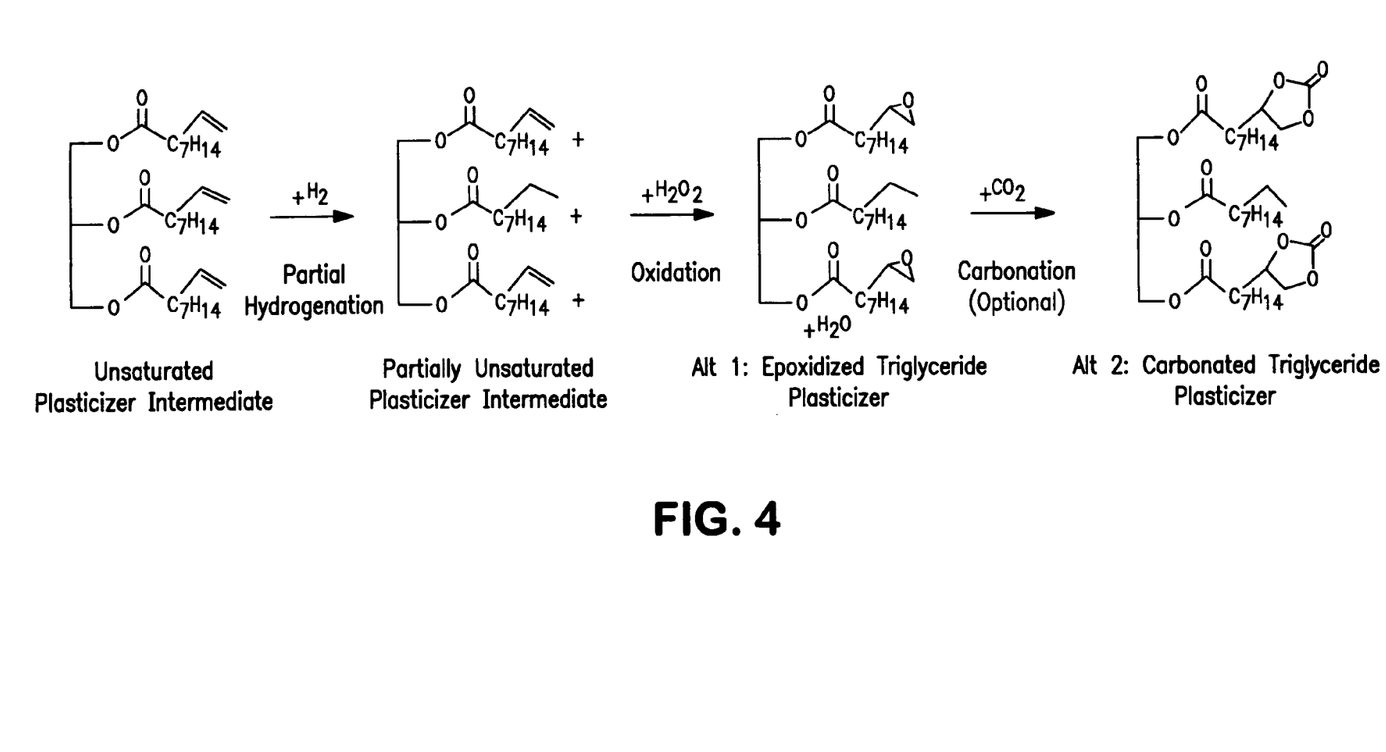
FIG. 4 schematically shows partial hydrogenation (of the second embodiment) of an unsaturated plasticizer intermediate, followed by epoxidation to produce an epoxidized triglyceride plasticizer. The figure also shows an optional carbonation of an epoxidized triglyceride plasticizer via reaction with carbon dioxide to produce carbonated triglyceride plasticizer.

The applicability of the triglyceride structures shown in FIG. 4 as potential PVC plasticizers can be screened by estimating their relative solubility in PVC using Small's group contribution method to calculate solubility parameters for each structure. (see The Technology of Plasticizers by J. Sears and J. Darbey, John Wiley & Sons, New York, 1982, pp 95-99, discussing using the Small formula to look at plasticizer compatibility with PVC; this paper cites as a reference, the original work by Small: Small, P. A., "Some Factors Affecting the Solubility of Polymers", J. Appl. Chem., 3, pp 76-80 (1953); see also using Small's group contribution values from the Polymer Handbook, 3rd Ed., J. Brandrup & E. H. Immergut, Eds. John Wiley, New York, (1989)). These calculations are shown below in Table 2:

TABLE 2

Solubility Data

| Solubility | Solubility Number | Solubility Contribution | MW | MW Contribution |
|---|---|---|---|---|
| Unsaturated Triglyceride | | | | |
| —CH2— | 133 | 24 | 3192 | 14 | 336 |
| COO esters | 310 | 3 | 930 | 44 | 132 |
| Terminal Double Bonds | 301 | 3 | 903 | 27 | 81 |
| | | | 5025 | | 549 |

Solubility Parameter = 9.09
Density = 0.993
Delta to PVC = −0.57

| Triglyceride Triepoxide | | | | |
|---|---|---|---|---|
| —CH2— | 133 | 24 | 3192 | 14 | 336 |
| COO esters | 310 | 3 | 930 | 44 | 132 |
| Epoxide ends | 416 | 3 | 1248 | 43 | 129 |
| | | | 5370 | | 597 |

Solubility Parameter = 8.93
Density = 0.993
Delta to PVC = −0.73

| Triglyceride Tricarbonate | | | | |
|---|---|---|---|---|
| —CH2— | 133 | 24 | 3192 | 14 | 336 |
| COO esters | 310 | 3 | 930 | 44 | 132 |
| Carbonate ends | 486 | 3 | 1458 | 87 | 261 |
| | | | 5580 | | 729 |

Solubility Parameter = 7.60
Density = 0.993
Delta to PVC = −2.06

The solubility parameter of PVC is calculated by the same method as described by Small to be 9.66. The differences in solubility parameters between the triglyceride structures in FIG. 3 and PVC are shown in Table 2. These differences from PVC range from 0.57 to 2.06 units, which indicate reasonable expected solubility in PVC. As references, the solubility parameters for two well known phthalate plasticizers, DINP (di-isononyl phthalate) and DIDP (di-isodecyl phthalate) are 8.88 (delta to PVC=0.78), and 8.56 (delta to PVC=1.10), respectively. The estimated solubility parameter for one non-phthalate plasticizer, di-isononyl cyclohexanoate is 7.32 by Small's method. This is a difference of 2.34 solubility parameter units from PVC, yet di-isononyl cyclohexanoate still is marketed commercially as a PVC plasticizer. Thus, based on their estimated solubility in PVC based on Small's method, the metathesized soybean oil based plasticizer structures shown in FIG. 4 can be expected to have reasonable utility as plasticizers for PVC as their estimated solubility parameters are in ranges similar to those of commercial plasticizers.

In one aspect of the second embodiment, the triglyceride plasticizers described herein may be used as plasticizers in polymer blends. The triglyceride plasticizers are used in a sufficient amount for the purpose of processing the polymer into a final article (such as a toy) or intermediate article (such as a pellet or powder) or in an amount required to provide the finished article with the desired amount of softness or flexibility. One skilled in the art may determine the appropriate amount without more than routine experimentation. Maximum and minimum amounts will vary depending on the polymer, additives and process selected, among other reasons. Polymer blends typically contain from about 0.1 wt % to about 45.0 wt % plasticizer, about 1 wt % to about 15.0 wt %, or about 5 wt % to about 10.0 wt %. The polymer blends may comprise about 99.9 to about 30 wt % of the polymers. Particularly useful for such purpose would be triglyceride plasticizers having properties of low volatility (<15% weight loss from 50 phr PVC blend over 7 days at 100° C.), good compatibility (no exudation of plasticizer from polymer blend), and good plasticizing ability (Shore A Hardness <85 at 50 wt %).

Some improved properties of the plasticizers of this embodiment (i.e., the inventive materials) relative to phthalate benchmark plasticizers are described below. The inventive materials are nontoxic, and they have a high plasticization efficiency. They are equivalent in volatility, low temperature property and plasticization efficiency to the benchmark dioctylphthalate plasticizer, and are about 10% more effective than current commercial non-phthalate plasticizer (di-isononylcyclohexanoate). This would enable one to use about 10% less of the inventive material, than of the cyclohexanoate, to achieve equivalent or the same plasticization (flexibility), in a polymer combined with the inventive material. Furthermore, the inventive materials have excellent low temperature properties, i.e.:

Clash Berg T for a plasticizer made from $C_7$ triglyceride is −32° C. versus −24° C. for the dioctylphthalate plasticizer;

Bell brittleness temperature for $C_7$ triglyceride is −43° C. versus −33° C. for the dioctylphthalate plasticizer.

The plasticizers of this embodiment also have excellent UV stability; thus PVC containing such plasticizer is expected to have more resistance to darkening upon exposure to UV.

Polymers blended with the inventive materials of this aspect of the disclosure may include polymers of polar monomers, or monomers containing heteroatoms, including but not limited to, PVC, polyamides, polyesters, polynitrile resins, ethylene vinyl acetate, polyvinyl butyrals, polystyrenes, polyurethanes, acrylics, brominated rubbers, and chlorinated rubbers. Polyolefins that may also be blended with the inventive materials include, for example, homopolymers and copolymers of $C_2$ to $C_{20}$ olefins (e.g., including ethylene, propylene, butene, hexene, and octene). A non-exclusive list of the polyolefins includes polyethylene, polypropylene, polybutene, ethylene propylene rubber, ethylene propylene diene monomer rubber, and similar polyolefins. Useful polyolefins have a weight average molecular weight (determined by GPC, polystyrene standards) of about 5,000 to about 1,000,000, such as about 50,000 to about 500,000. Useful polymers include plastics, thermoplastics, plastomers and elastomers.

A group of polymers that may be blended with the inventive materials includes polar polymers, such as engineering resins, particularly those described in PCT Patent Publication No. WO2007/050071, e.g., at pages 22 to 24 incorporated herein by reference. Useful engineering resins are thermoplastic polymers, copolymers or mixtures thereof, having a Young's modulus (ASTM D 412-92, room temperature) of more than about 500 MPa and a melting point (DSC, second melt, 10° C./min) of about 170° C. to about 230° C.

The compositions described herein, particularly those comprising polymers blended with the inventive materials, may further comprise additives, such as carbon black, adhesion promoters, viscosity depressants, pigments, colorants, fillers, such as calcium carbonate fillers, Ca/Zn or Ba/Zn stabilizers, lubricants, pigments and dyes or other colorants, antioxidants or other stabilizers and mixtures thereof.

The compositions of this embodiment can be processed into products through rotomolding, dipping, spraying, spreading, molding, extrusion, calendering, and injection molding, as well as by processing plastisols.

The compositions of this embodiment can further comprise additional plasticizers, selected from, but not limited to, at least one plasticizer selected from phthalates, adipates, trimellitates, cyclohexanoates, cyclohexadionates, benzoates, citrates, terephthalates, adipates and polymeric plasticizers.

The present disclosure will now be illustrated with reference to the following non-limiting Examples and the accompanying drawings, without limiting the scope of the disclosure.

EXAMPLES

Examples 1 & 2 are directed to an integrated method of making synthetic hydrocarbon fluids. Examples 3 & 4 are directed to an integrated method of producing synthetic lubricant base stocks and plasticizers.

Example 1

Metathesis of Methyl Oleate with Ethylene to Produce Olefins and Reduced Chain Length Triglycerides (e.g. Methyl Ester) (First Embodiment)

30 gram of technical grade methyl oleate (70% purity with 30% of other methyl esters, available from Aldrich) was purified by degassing to remove dissolved oxygen and dried over 5 A molecular sieve. The purified methyl oleate (MO) was charged into a 300 ml autoclave under $N_2$ atmosphere. The reactor was pressurized with ethylene gas to about 200 psig while maintaining it at about 23° C. or below. A metathesis catalyst solution containing 90 mg of [1,3-bis-(2,4,6-trimethylphenyl)-2-imidazolidinylidene]dichloro-(phenylmethylene)-(tricyclohexylphosphine)ruthenium] (Catalyst formula 2, $2^{nd}$ generation Grubbs Catalyst) in 20 ml toluene was charged into the reactor under $N_2$ pressure. The final reactor pressure was raised with ethylene to about 500 psi. The reaction proceeded for a total of 20 hours at room temperature. The reaction product was analyzed by a gas chromotograph equipped with a 60 meter boiling point DB1 capillary column available from J&W of Folsom, Calif. The product distribution showed that MO underwent cross-metathesis with ethylene to produce linear alpha-olefins (LAO), mostly 1-decene with some amount of $C_6$ to $C_{12}$ LAOs, and methyl 9-decenoate. MO also underwent self-metathesis to produce 9-octadecene and dimethyl 9-octadecen-di-oate. The detailed product distribution is summarized in Table 3.

Example 2

Metathesis of Natural Oil with Ethylene to Produce Olefins and Reduced Chain Length Triglycerides (First Embodiment)

This example was similar to Example 1, except a typical canola oil produced from Canadian rapeseed oil, which is reported to be used as feed for biodiesel, was purified similarly as the methyl oleate. The product distribution showed that the vegetable oil underwent cross-metathesis with ethylene to produce LAO, mostly 1-decene with smaller amounts of $C_6$ to $C_{12}$ LAOs, and triglycerides. The vegetable oil also underwent self-metathesis to produce 9-octadecene and 7-pentadecene and oligo-triglyceride. Detailed product distribution is summarized in Table 3.

TABLE 3

Reaction Product Analysis by GC

| Example 1 | | Example 2 | |
|---|---|---|---|
| Feed Type | methyl oleate | Feed Type | Canola Oil |
| Feed Weight, g | | Feed Weight, g | |
| Conversion, wt % | 58.43 | Conversion, wt % | 20.42 |
| % Selectivity to Product | | % Selectivity to product | |
| $C_2$-$C_5$ | 1.3 | $C_2$-$C_5$ | 4.12 |
| $C_6$-$C_{10}$-LAO | 17.2 | $C_6$-$C_{10}$-LAO | 40.55 |
| $C_{10}$-$C_{18}$ internal olefins | 32.8 | $C_{10}$-$C_{18}$ internal olefins | 53.51 |
| $C_{10}$-$C_{12}$ ME Products | 15.4 | Triglycerides | not observed on GC |
| $C_{18}$ DE | 22.5 | $C_{18}$ DE | 1.82 |
| $C_{19}$-$C_{22}$ DE | 10.8 | | |

ME = mono-methyl ester
DE = di-methyl ester

Example 3

Oligomerization of Olefins from Example 1 to Produce High Performance Lubricant Base Stocks In this set of experiments, 1-decene, the major LAO produced from the metathesis reaction and 9-octadecene, the major internal olefin produced from the metathesis reaction, were polymerized individually, or co-polymerized in the presence of $AlCl_3$ catalyst. Four experiments were conducted:
  3A—polymerization of 9-octadecene;
  3B—copolymerization of 9-octadecene and 1-decene;
  3C—copolymerization of 9-octadecene and 1-decene;
  3D—polymerization of 1-decene.
In these experiments, the feed olefins, 20 grams each, of the LAO (the 1-decene) and the internal olefin (the 9-octadecene) were individually (or together, as discussed below) were charged into respective round bottom flasks with stifling. Then 0.6 gram solid $AlCl_3$ was added to the olefin (or the mixture of olefins) with periodic cooling to control temperature at room temperature. The reaction was allowed to proceed for 4 hours. The reaction mixture was then poured into 50 ml 5% sodium hydroxide solution and stirred for 15 minutes. The aqueous layer was separated. The organic layer was washed with 50 ml water three times. The organic layer was dried by solid sodium sulfate and then fractionated under high vacuum to remove unreacted olefins and any light fraction. The residual clear polymer liquid was obtained in 60 to 95% lube yield. The lube properties are summarized in the following Table. Example 3A was made from 9-octadecene with high internal olefin content. The resulting synthetic hydrocarbon fluid had excellent viscosity, 12.73 cS at 100° C., 140 VI and −43° C. pour point. These were outstanding properties, favorably comparable to the PAO made from pure LAO 1-decene (Example 3D). When a mixture of 1-decene LAO and internal olefin 9-octadecene was used as feed, as in Examples 3B and 3C, the lube products had superior viscosities, VI and pour points. Examples 3A to 3D were not hydrogenated. The as synthesized lubes had bromine number >2. This bromine number can be reduced to <2 by hydrogenation. The lube properties are not expected to change significantly after hydrogenation.

| | Example 3 | | | |
|---|---|---|---|---|
| | A | B | C | D |
| Feed Composition, Wt % | | | | |
| 1-Decene | 0.0 | 32.7 | 65.4 | 98.0 |
| 9-Octadecene | 97.1 | 65.4 | 32.7 | 0.0 |
| Product Property | | | | |
| 100° C. Kv, cS | 12.73 | 16.82 | 27.75 | 26.34 |
| 40° C. Kv, cS | 89.46 | 127.30 | 237.95 | 231.44 |
| VI | 140 | 143 | 152 | 146 |
| Pour Point (D5949-21), ° C. | −43 | −41 | −33 | −34 |
| Bromine Number | 12.8 | 15.9 | | |

These data demonstrated the unexpected advantageous properties of the PAO or the synthetic hydrocarbon fluids produced from the olefins from metathesis chemistry of triglycerides or fatty acid esters, in accordance with this disclosure.

Example 4

Isolation of the Reduced Chain Length Triglycerides and their Hydrogenation and Isomerization to Produce High Performance Plasticizers or Gr V Base Stocks The reduced chain length triglycerides contain glycerol esters of $C_6$ to $C_{12}$ unsaturated acids. These glycerol esters can be hydrogenated to produce fully saturated glycerol esters. An example of this type of glycerol esters of n-$C_8$ and $C_{10}$ mixed acids have the following lube properties: 100° C. Kv=3.44 cS, 40° C. Kv=13.84 cS, VI=127, pour point=−18° C., Noack volatility=5.25 wt %. These properties are much better than those of other commonly available dibasic synthetic ester fluids or phthalic ester fluids. The glycerol esters, expected to be produced according to processes described herein, are expected to have outstanding thermal, oxidative and hydrolytic stability, significantly better than the naturally occurring triglycerides or esters.

Applicants have attempted to disclose all embodiments and applications of the disclosed subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All patents, test procedures, and other documents cited herein, including priority documents, are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

What is claimed is:

1. An integrated method for making synthetic hydrocarbon fluids and/or polar functional fluids comprising:
   (a) contacting a feed selected from one or more natural oils, which includes one or more triglycerides, one or more mono-esters derived from one or more triglyceride, or a mixture thereof, each of the natural oils and mono-esters including linear $C_{12}$ to $C_{30}$ unsaturated fatty acid moieties, with ethylene in the presence of an effective amount of a metathesis catalyst to form linear alpha-olefins, internal olefins and reduced chain length triglyceride or triglycerides, or reduced chain length mono-esters derived from one or more triglycerides, wherein the contacting is carried out at an ethylene partial pressure of 0 psig to 3,000 psig,
   (b) polymerizing the linear alpha-olefins, the internal olefins or a mixture thereof in the presence of a suitable catalyst to produce one or more oligomeric synthetic hydrocarbon fluids, wherein the one or more oligomeric synthetic hydrocarbon fluids is a copolymer of linear alpha-olefins and internal olefins or a polymer of linear alpha-olefins or a polymer of internal olefins.

2. The method of claim 1, wherein the one or more natural oils is chosen from plant oil, vegetable oil, animal oil, $C_1$- to $C_5$-alkyl ester of the fatty acids derived from plant oil, vegetable oil and animal oil.

3. The method of claim 1, wherein the metathesis catalyst is chosen from the halides and organometallic compounds of tungsten, molybdenum, ruthenium, tantalum, and rhenium.

4. The method of claim 1, wherein the metathesis catalyst is chosen from a Grubbs catalyst of first generation, a Grubbs catalyst of second generation and a Hoveyda-Grubbs catalyst.

5. The method of claim 1, wherein the metathesis catalyst is an activated $WCl_6$ or $MoCl_6$ or $TaCl_5$ or $Re_2O_7$ on a solid support.

6. The method of claim 5, wherein the solid support is $Al_2O_3$, $ZrO_2$, $Ta_2O_5$, $SiO_2$, $WO_3$, or $SiO_2/Al_3$.

7. The method of claim 5, wherein the metathesis catalyst is activated by:
   i. a compound of the formula $AlR_aX_b$, wherein R is $C_1$-$C_6$ alkyl, X is a halide or an alkoxide, a+b=3, and each of a and b=1 to 3; or
   ii. a compound of the formula $SnR_cX_d$, wherein R is $C_1$-$C_6$ alkyl, X is a halide or an alkoxide, c+d=4, and each of c, d=1 to 4.

8. The method of claim 1, wherein the contacting is carried out at a temperature between 0° C. and 300° C.

9. The method of claim 1, wherein the contacting is carried out for a reaction period of 5 minutes to 1440 minutes, 10. The method of claim 1, wherein the suitable catalyst to produce the one or more oligomeric synthetic hydrocarbon fluids is $AlCl_3$, $BF_3$, or promoted $AlCl_3$.

11. The method of claim 1, wherein the suitable catalyst to produce the one or more oligomeric synthetic hydrocarbon fluids is one or more metallocene catalyst systems promoted by a non-coordinating anion or methylaluminoxane or an activated $CrO/SiO_2$ catalyst or an activated Ziegler catalyst.

12. The method of claims 1, 9 or 10, wherein the one or more oligomeric synthetic hydrocarbon fluids have a 100° C. Kv of greater than 2 cS, a VI of greater than 80, and a pour point of less than 0° C.

13. The method of claim 1, wherein the linear alpha-olefins are produced by a cross-metathesis reaction.

14. The method of claim 1, wherein a substantial portion of the internal olefins is produced by a self-metathesis reaction of the one or more triglycerides or the one or more esters derived from one or more triglycerides.

15. The method of claim 1, further comprising hydrogenation or isomerization followed by hydrogenation, of the reduced chain length triglyceride or triglycerides to produce one or more polar synthetic lubricant base stocks or one or more plasticizers.

16. The method of claim 1, further comprising hydroisomerization of the reduced chain length triglyceride or triglycerides to produce one or more polar synthetic lubricant base stocks or one or more plasticizers.

17. The method of claims 15 or 16, wherein the one or more polar synthetic lubricant base stocks comprise glycerol esters of fully saturated $C_6$ to $C_{14}$ fatty acids with linear or branched carbon chains or with a mixture of linear and branched carbon chains.

18. The method of claims 15 or 16, wherein the one or more polar synthetic lubricant base stocks have a 100° C. Kv of 2 cS to 20 cS, a VI greater than 80, and a Noack volatility of 20% or less, and better oxidative stability than the one or more natural oils or the one or more mono-esters.

19. The method of claims 15 or 16, wherein the one or more plasticizers comprise medium chain length triglycerides produced by methathesis.

* * * * *